(12) United States Patent
McGuire et al.

(10) Patent No.: US 12,030,831 B2
(45) Date of Patent: Jul. 9, 2024

(54) PROCESS FOR THE ALKYLATION OF ALIPHATIC ORGANIC COMPOUNDS

(71) Applicant: BASF SE, Ludwigshafen am Rhein (DE)

(72) Inventors: Robert McGuire, Florham Park, NJ (US); Andrei-Nicolae Parvulescu, Ludwigshafen (DE); Ulrich Mueller, Ludwigshafen (DE); Dirk De Vos, Leuven (BE); Patrick Tomkins, Leuven (BE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/765,620

(22) PCT Filed: Dec. 20, 2018

(86) PCT No.: PCT/EP2018/086229
§ 371 (c)(1),
(2) Date: May 20, 2020

(87) PCT Pub. No.: WO2019/122147
PCT Pub. Date: Jun. 27, 2019

(65) Prior Publication Data
US 2020/0308083 A1  Oct. 1, 2020

(30) Foreign Application Priority Data
Dec. 21, 2017  (EP) .................... 17209768

(51) Int. Cl.
  *C07C 2/58*  (2006.01)
  *B01J 29/70*  (2006.01)
(52) U.S. Cl.
  CPC ............. *C07C 2/58* (2013.01); *B01J 29/7007* (2013.01); *C07C 2529/70* (2013.01)

(58) Field of Classification Search
None
See application file for complete search history.

(56) References Cited

U.S. PATENT DOCUMENTS

| | | | |
|---|---|---|---|
| 4,992,616 A | | 2/1991 | Chou et al. |
| 5,705,729 A | * | 1/1998 | Huang ...................... C07C 2/58 |
| | | | 585/709 |

(Continued)

FOREIGN PATENT DOCUMENTS

| CN | 104557939 A | 4/2015 |
|---|---|---|
| JP | H04-502756 A | 5/1992 |

(Continued)

OTHER PUBLICATIONS

Nivarthy et al. "The influence of acidity on zeolite H-BEA catalyzed isobutane/n-butene alkylation" Microporous and Mesoporous Materials 22 (1998) 379-388. (Year: 1998).*

(Continued)

*Primary Examiner* — In Suk C Bullock
*Assistant Examiner* — Alyssa L Cepluch
(74) *Attorney, Agent, or Firm* — DLA Piper LLP (US)

(57) ABSTRACT

Disclosed is a process for the alkylation of an aliphatic organic compound comprising: (a) providing a catalyst comprising one or more zeolitic materials having a BEA framework structure, wherein the BEA framework structure comprises $YO_2$ and optionally comprises $X_2O_3$, wherein Y is a tetravalent element, and X is a trivalent element, (b) contacting the catalyst with one or more aliphatic organic compounds in the presence of one or more alkylating agents in one or more reactors for obtaining one or more alkylated organic compounds, wherein the one or more zeolitic materials are obtainable from a synthetic process which does not employ an organotemplate as structure directing agent.

12 Claims, 6 Drawing Sheets

(56) References Cited

U.S. PATENT DOCUMENTS 5,824,835 A 10/1998 Agaskar et al.
2012/0259148 A1 10/2012 Yilmaz et al.

FOREIGN PATENT DOCUMENTS

| WO | 90/00533 | 1/1990 |
| WO | WO 2010/146156 A1 | 12/2010 |
| WO | WO 2012/137133 A1 | 10/2012 |

OTHER PUBLICATIONS

Nivarhty, G.S. et al., "Alkylation of isobutane with light olefins catalyzed by zeolite beta," Microporous and Mesoporous Materials, 2000, vol. 35-36, XP004194454, pp. 75-87.

Nivarhty, G.S. et al., "The influence of acidity on zeolite H-BEA catalyzed isobutane/n-butane alkylation," Microporous and Mesoporous Materials, Jun. 17, 1998, vol. 22, No. 1-3, XP004128339, pp. 379-388.

Kato, Y. et al., "Alkylation of Isobutane by 1-Butene over H-beta Zeolite in CSTR (Part 3) Effect of Property of H-Beta Zeolite," Journal of Japan Petroleum Institute, 2013, vol. 56, No. 5, XP002781573, pp. 349-355.

International Preliminary Report on Patentability dated Mar. 10, 2020 in PCT/EP2018/086229 filed on Dec. 20, 2018.

International Search Report dated Mar. 1, 2019 in PCT/EP2018/086229 filed on Dec. 20, 2018.

Notice of Reasons for Refusal from corresponding Japanese Appln. No. 2020-534890 dated Feb. 7, 2023, and a machine generated translation.

* cited by examiner

PROCESS FOR THE ALKYLATION OF ALIPHATIC ORGANIC COMPOUNDS

The present invention relates to a process for the alkylation of an aliphatic organic compound using a catalyst comprising one or more zeolitic materials having a BEA framework structure, wherein the zeolitic material is obtainable from a synthetic process which does not employ an organotemplate as structure directing agent.

INTRODUCTION

Highly branched $C_7$ and $C_8$ alkanes exhibit excellent fuel properties and can be produced by the alkylation of isobutane using propene or butenes (see FIG. 1). On an industrial scale, this alkylation is currently based on hydrofluoric or sulfuric acid; so far no solid catalyst was found to replace the liquid acids. Although several active solid catalysts are known, stability is still the major challenge. So far the most promising catalysts were La- and Ce-exchanged FAU type zeolites and different H-form zeolites, where zeolite beta shows good results. Thus, Feller, A. et al. in Journal of Catalysis, 2004, Vol. 224, pp. 80-93 relates to the alkylation of isobutane with butene over zeolites X and Y in their acidic form. Dalla Costa, B. O. et al. in Applied Catalysis A 2010, Vol. 385, pp. 144-152 and Corma, A. et al. in Applied Catalysis A 1994, Vol. 119, pp. 83-96, on the other hand, respectively concern the alkylation of isobutane with butenes over solid catalysts based on zeolite beta. There however remains the ongoing challenge to balance the acid strength however also remains, as too strong acid sites promote cracking and too weak acid sites elicit the dimerization of the olefin.

Zeolite beta catalysts are also known to be used in the alkylation of aromatic organic compounds. In this respect, WO 2012/137133 A concerns the use of zeolite beta as the solid catalyst, wherein zeolite beta has been obtained from a synthetic process which does not employ an organotemplate. In particular, although the results indicate a lower activity of the zeolites compared to commercial zeolite beta as obtained from templated synthesis, the selectivity towards monoalkylated products is higher. Furthermore, as regards the monoalkylated products, an increase in regioselectivity is observed compared to commercial zeolite beta.

With regard to the alkylation of aliphatic organic compounds, there remains the need for an improved catalyst, in particular in view of the aforementioned problems of catalyst stability and side reactions observed with the current solid catalysts.

U.S. Pat. Nos. 4,992,616 A and 5,824,835 A respectively relate to a heterogeneous catalysis process for the alkylation of olefins with isoparaffins. Nivarthy, G. S. et al. in Microporous and Mesoporous Materials 2000, vol. 35-36, pages 75-87, concerns the alkylation of isobutane with light olefins in a reaction catalyzed by zeolite beta. Nivarthy, G. S. et al. in Microporous and Mesoporous Materials 1998. vol. 22, no. 1-3, pages 379-388, on the other hand, relates to the influence of acidity on the zeolite beta catalyzed reaction of isobutane with light olefins. Yuki Kato et al. in Journal of the Japan Petroleum Institute 2013, vol. 56, no. 5, pages 349-355, for their part relate the alkylation of isobutane by 1-butene over zeolite beta in its H-form.

DETAILED DESCRIPTION

Accordingly, it was the object of the present invention to provide an improved process for the alkylation of aliphatic organic compounds. Thus, it has surprisingly been found that such processes involving the use of a catalyst comprising zeolitic materials having a BEA framework structure, and in particular zeolite beta, may be considerably improved by using a zeolitic material therein which is obtainable from a synthetic process which does not employ an organotemplate as structure directing agent. In particular, it has quite surprisingly been found that by using such a zeolitic material, the activity of the alkylation catalyst may be increased to an extent which would not have been expected considering the activity of a commercial zeolitic material having a BEA framework structure as obtained from a templated synthetic methodology. Thus, as demonstrated in the experimental section of the present application, although an increase in activity may be observed with decreasing Si:Al molar ratio of the framework structure in the latter, the increase in activity which may be achieved when using zeolitic materials having a BEA framework as obtained from a synthetic process which does not employ an organotemplate, in particular at low Si:Al molar ratio of the framework structure, greatly surpasses the tendencies which may be observed for commercial zeolites having a BEA framework structure. Furthermore and even more unexpectedly, it has surprisingly been found that the selectivity of the alkylation reaction employing a zeolitic material having a BEA framework structure as obtainable from an organotemplate-free synthetic method towards the products of the reaction having the same number of carbon atoms as the sum of the carbon atoms of the alkylating agent and the aliphatic organic compound is significantly higher than when employing a commercial zeolitic material having a BEA framework structure. In particular, as demonstrated in the experimental section of the present application, this phenomenon is no linked to particularly low Si:Al molar ratios, but may be observed also at higher Si:Al molar ratios as well.

Thus, the present invention concerns a process for the alkylation of an aliphatic organic compound comprising:
(a) providing a catalyst comprising one or more zeolitic materials having a BEA framework structure, wherein the BEA framework structure comprises $YO_2$ and optionally comprises $X_2O_3$, wherein Y is a tetravalent element, and X is a trivalent element,
(b) contacting the catalyst with one or more aliphatic organic compounds in the presence of one or more alkylating agents in one or more reactors for obtaining one or more alkylated organic compounds,
wherein the one or more zeolitic materials are obtainable from a synthetic process which does not employ an organotemplate as structure directing agent.

According to the present invention, the term "organotemplate" and "organic structure directing agent" are used synonymously, wherein the term "organotemplate" or "organic structure directing agent" refers to any organic compound, and preferably to any organic compound containing an organocation, which may be added to a synthetic process for the preparation of a zeolitic material having a BEA framework structure as structure directing agent. Furthermore, the term "organotemplate-free" as used in the present application refers to a synthetic process which does not employ an organotemplate as structure directing agent, i.e. which is organotemplate-free, wherein said terms define synthetic processes for the preparation of a zeolitic material having a BEA framework structure wherein at no point in the process does the reaction mixture contain more than 1 wt.-% of an organic structure directing agent based on 100 wt.-% of $YO_2$ contained in the reaction mixture, preferably more than 0.5 wt.-%, more preferably more than 0.1 wt.-%, more preferably more than 0.05 wt.-%, more preferably more than 0.01 wt.-%, more preferably more than 0.005 wt.-% or less, more preferably more than 0.001 wt.-%, more preferably more than 0.0005 wt.-% or less, and more preferably more than 0.0001 wt.-% of an organic structure directing agent based on 100 wt.-% of $YO_2$ contained in the reaction mixture.

According to the present invention, there is no particular restriction as to the number and/or types of zeolitic materials which are provided as a catalyst in step (a) of the inventive process, provided that the have the BEA framework structure and at least comprise $YO_2$, and provided that they are suited for catalyzing the alkylation of an aliphatic organic compound as defined in the respective embodiments and/or preferred embodiments of the present invention. Thus, by way of example, the one or more zeolitic materials may comprise one or more zeolites selected from the group consisting of zeolite Beta, [B—Si—O]-BEA, [Ga—Si—O]-BEA, [Ti—Si—O]-BEA, Al-rich beta, CIT-6, tschernichite, and pure silica beta, wherein preferably the one or more zeolitic materials comprise zeolite beta. Again, among the zeolite beta preferably comprised in the one or more zeolitic materials, there is no particular restriction as to which specific type thereof may be used, provided that it is obtainable from a synthetic process which does not employ an organotemplate.

It is, however, further preferred according to the present invention that the one or more zeolitic materials comprised in the catalyst of the inventive process consists of one or more zeolitic materials having a BEA framework structure according to any of the particular or preferred embodiments of the present invention, wherein more preferably the one or more zeolitic materials comprised in the catalyst of the inventive process consists of zeolite beta according to any of the particular or preferred embodiments of the present invention. According to the present invention it is yet further preferred that the catalyst of the inventive process consists of one or more zeolitic materials having a BEA framework structure according to any of the particular or preferred embodiments of the present invention, wherein more preferably the catalyst of the inventive process consists of zeolite beta according to any of the particular or preferred embodiments of the present invention.

Thus, according to the present invention, it is preferred that the one or more zeolitic materials provided as a catalyst in step (a) comprise zeolite beta, wherein preferably the one or more zeolitic materials are zeolite beta, and wherein more preferably zeolite beta is used as the one or more zeolitic materials.

In principle, the one or more zeolitic materials having a BEA framework structure which are employed in the inventive process may be obtained by any conceivable synthetic process, provided that it may equally be obtained from a process which does not employ an organotemplate as structure directing agent. Preferably, the one or more zeolitic materials having a BEA framework structure are obtained from a synthetic process which does not employ an organotemplate as structure directing agent. In Xiao et al., Chem. Mater. 2008, 20, pp. 4533-4535 and Supporting Information, for example, a process for the synthesis of zeolite beta is described, in which crystallization of an aluminosilicate gel is conducted using zeolite beta seed crystals. In this respect, WO 2010/146156 A may also be mentioned, which relates to organotemplate-free synthesis of zeolitic materials having the BEA framework structure, and in particular to the organotemplate-free synthesis of zeolite beta. In Majano et al., Chem. Mater. 2009, 21, pp. 4184-4191, on the other hand, Al-rich zeolite beta materials having Si/Al ratios as low as 3.9 are discussed which may be obtained from reactions employing seeding in the absence of organic templates.

According to the present invention, the one or more zeolitic materials provided as a catalyst in step (a) preferably do not contain more than an impurity of an organic structure directing agent typically used in the synthesis of zeolitic materials having a BEA framework structure, in particular specific tetraalkylammonium salts and/or related organotemplates such as tetraethylammonium and/or dibenzylmethylammonium salts, and dibenzyl-1,4-diazabicyclo[2,2,2]octane. Such an impurity can, for example, be caused by organic structure directing agents still present in seed crystals used in the preferred synthetic process. According to the present invention, an impurity of an organotemplate or of an organic structure directing agent refers to an amount of 1 wt.-% or less based on 100 wt.-% of $YO_2$ contained in the one or more zeolitic materials, and preferably of 0.5 wt.-% or less, more preferably 0.1 wt.-% or less, more preferably 0.05 wt.-% or less, more preferably 0.01 wt.-% or less, more preferably 0.005 wt.-% or less, and more preferably of 0.001 wt.-% or less of an organic structure directing agent contained in the one or more zeolitic materials.

Furthermore, it is preferred according to the present invention that the one or more zeolitic materials having a BEA framework structure are non-calcined, meaning that they have not been subject to a calcination step. Within the meaning of the present invention, a calcination step generally designates a process involving the heating of the one or more zeolitic materials above a temperature of 500° C. More preferably, however, a non-calcined zeolitic material according to the present invention designates a material not having been subject to a temperature exceeding 450° C., more preferably 350° C., more preferably 300° C., more preferably 250° C., more preferably 200° C., and even more preferably not exceeding 150° C. In general, a calcination step may designate any step which may be employed in the synthesis of the one or more zeolitic materials having a BEA framework structure used in the inventive process. According to the present invention, however, a calcination step preferably only refers to a step conducted after completion of the crystallization of the one or more zeolitic materials having a BEA framework structure from one or more precursor compounds which do not have a BEA framework structure, with the exception of any seeding crystals which may be employed therein. According to a yet further preferred embodiment of the present invention, a calcination step only refers to a step which is normally or suitably performed after completed crystallization of the one or more zeolitic materials for the removal of organotemplates from the framework structure.

Thus, according to the present invention it is preferred that the one or more zeolitic materials provided as a catalyst in step (a) of the inventive process are non-calcined.

Within the meaning of the present invention, $YO_2$ and optionally $X_2O_3$ comprised in the BEA framework structure of the one or more zeolitic materials are contained therein as structure building elements, as opposed to non-framework elements which can be present in the pores and cavities formed by the framework structure and typical for zeolitic materials in general.

According to the present invention, Y comprised in the one or more zeolitic materials having a BEA framework structure stands for any conceivable tetravalent element, wherein Y is one or more tetravalent elements. Preferred tetravalent elements according to the present invention include Si, Sn, Ti, Zr, and Ge, and combinations thereof. More preferably, Y stands for Si, Ti, or Zr, or any combination of said trivalent elements, even more preferably for Si and/or Sn. According to the present invention, it is particularly preferred that Y stands for Si.

Thus, according to the present invention it is preferred that Y comprised in the one or more zeolitic materials provided as a catalyst in step (a) is selected from the group consisting of Si, Sn, Ti, Zr, Ge, and combinations of two or more thereof, Y preferably being Si.

According to the present invention it is preferred that the framework of the one or more zeolitic materials having a BEA structure further comprises $X_2O_3$, wherein X stands for any conceivable trivalent element, wherein X is one or more trivalent elements. Preferred trivalent elements according to the present invention include Al, B, In, and Ga, and combinations thereof. More preferably, Y stands for Al, B, or In, or any combination of said trivalent elements, even more preferably for Al and/or B. According to the present invention, it is particularly preferred that X stands for Al.

Thus, according to the present invention it is preferred that X optionally comprised in the one or more zeolitic materials provided as a catalyst in step (a) is selected from the group consisting of Al, B, In, Ga, and combinations of two or more thereof, X preferably being Al.

According to the present invention it is preferred that the one or more zeolitic materials having a BEA framework structure provided as a catalyst in step (a) comprise $X_2O_3$ in addition to $YO_2$. In principle, with respect to said preferred embodiments, there is no particular restriction as to the Y:X molar ratio displayed by the one or more zeolitic materials such that in principle zeolitic materials having any conceivable and realizable Y:X molar ratio may be used. Thus, by way of example, the one or more zeolitic materials may display Y:X molar ratios ranging anywhere from 1 to 100, wherein preferably the Y:X molar ratio is comprised in the range of from 2 to 50, more preferably of from 2.5 to 30, more preferably of from 3 to 20, more preferably of from 3.5 to 15, more preferably of from 3.7 to 10, more preferably of from 3.9 to 8, more preferably of from 4.1 to 6, and even more preferably in the range of from 4.3 to 5.5. According to particularly preferred embodiments, the Y:X molar ratio of the one or more zeolitic materials provided as a catalyst in step (a) is comprised in the range of from 4.5 to 5.

Thus, according to embodiments of the present invention wherein X is comprised in the one or more zeolitic materials provided as a catalyst in step (a), the Y:X molar ratio thereof is preferably in the range of from 1 to 100, preferably of from 2 to 50, more preferably of from 2.5 to 30, more preferably of from 3 to 20, more preferably of from 3.5 to 15, more preferably of from 3.7 to 10, more preferably of from 3.9 to 8, more preferably of from 4.1 to 6, more preferably of from 4.3 to 5.5, and more preferably in the range of from 4.5 to 5.

According to the present invention, there is no particular restriction as to any further elements or compounds which may be contained in the one or more zeolitic materials having a BEA framework structure comprised in the catalyst of the inventive process. This applies both to the elements contained in the framework of the one or more zeolitic materials, as well as with regard to an non-framework elements or compounds which may be contained in the micropores of the one or more zeolitic materials, including counterions to the framework structure contained as non-framework elements in the micropores of the one or more zeolitic materials. According to the present invention it is preferred that the one or more zeolitic materials having a BEA framework structure contain $H^+$ as counterions to the framework of the one or more zeolitic materials, wherein It is further preferred according to the present invention that besides $H^+$ contained as counterions in the one or more zeolitic materials, the one or more zeolitic materials contain 5 wt.-% or less of non-framework elements based on 100 wt.-% of $YO_2$, preferably 3 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, and more preferably 0.001 wt.-% or less of non-framework elements based on 100 wt.-% of $YO_2$.

According to particular and preferred embodiments of the present invention wherein the one or more zeolitic materials comprised in the catalyst of the inventive process comprise non-framework elements or compounds, wherein preferably the non-framework elements comprise $H^+$ contained as counterions in the one or more zeolitic materials, there is no particular restriction as to the non-framework elements or compounds which may be contained therein, in particular in addition to $H^+$ preferably contained as counterions in the one or more zeolitic materials. It is, however, preferred according to the present invention that the one or more zeolitic materials contain 5 wt.-% or less of Na and/or K as non-framework elements based on 100 wt.-% of $YO_2$, preferably 3 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, and more preferably 0.001 wt.-% or less of Na and/or K as non-framework elements based on 100 wt.-% of $YO_2$. Furthermore, it is preferred that the one or more zeolitic materials contain 5 wt.-% or less of Li, Na, and K as non-framework elements based on 100 wt.-% of $YO_2$, preferably 3 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, and more preferably 0.001 wt.-% or less of Li, Na, and K as non-framework elements based on 100 wt.-% of $YO_2$. Yet further it is preferred that the one or more zeolitic materials contain 5 wt.-% or less of alkali metals as non-framework elements based on 100 wt.-% of $YO_2$, preferably 3 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, and more preferably 0.001 wt.-% or less of alkali metals as non-framework elements based on 100 wt.-% of $YO_2$. Yet further it is preferred that the one or more zeolitic materials contain 5 wt.-% or less of alkali and alkaline earth metals as non-framework elements based on 100 wt.-% of $YO_2$, preferably 3 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, and more preferably 0.001 wt.-% or less of alkali and alkaline earth metals as non-framework elements based on 100 wt.-% of $YO_2$. Yet further it is preferred that the one or more zeolitic materials contain 5 wt.-% or less of alkali, alkaline earth, and transition metals as non-framework elements based on 100 wt.-% of $YO_2$, preferably 3 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, and more preferably 0.001 wt.-% or less of alkali, alkaline earth, and transition metals as non-framework elements based on 100 wt.-% of $YO_2$. Yet further it is preferred that the one or more zeolitic materials contain 5 wt.-% or less of metals as non-framework elements based on 100 wt.-% of $YO_2$, preferably 3 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, and more preferably 0.001 wt.-% or less of metals as non-framework elements based on 100 wt.-% of $YO_2$.

According to the present invention, there is no particular restriction as to the crystalline structure of the one or more zeolitic materials provided as a catalyst in step (a) of the inventive process, provided that these display a BEA framework structure, and, in particular, that the one or more zeolitic materials afford an X-ray diffraction pattern comprising the reflections typical of a BEA framework structure. Within the meaning of the present invention, an X-ray pattern typical of a BEA framework structure primarily designates a pattern of reflections comprised in an x-ray diffractogram, wherein the 2θ diffraction angles are typical of a BEA framework structure, and wherein preferably also the relative intensities of the individual reflections are typical of a BEA framework structure. According to particularly preferred embodiments of the present invention, the one or more zeolitic materials having a BEA framework structure display an X-ray diffraction pattern comprising at least the following reflections:

| Intensity (%) | Diffraction angle 2θ/° [Cu K(alpha 1)] |
|---|---|
| [9-29] | [21.06-21.26] |
| 100 | [22.11-22.31] |
| [10-30] | [25.01-25.21] |
| [8-28] | [26.77-26.97] |
| [12-32] | [28.38-28.58] |
| [27-47] | [29.22-29.42] |
| [7-27] | [29.99-30.19] |
| [9-29] | [32.85-33.25] |
| [11-31] | [42.86-43.26] | wherein 100% relates to the intensity of the maximum peak in the X-ray powder diffraction pattern.

More preferably, the one or more zeolitic materials having a BEA framework structure display an X-ray diffraction pattern comprising at least the following reflections:

| Intensity (%) | Diffraction angle 2θ/° [Cu K(alpha 1)] |
|---|---|
| [9-29] | [21.11-21.21] |
| 100 | [22.16-22.26] |
| [10-30] | [25.06-25.16] |
| [8-28] | [26.82-26.92] |
| [12-32] | [28.43-28.53] |
| [27-47] | [29.27-29.37] |
| [7-27] | [30.04-30.14] |
| [9-29] | [33.00-33.10] |
| [11-31] | [43.01-43.11] | wherein 100% relates to the intensity of the maximum peak in the X-ray powder diffraction pattern.

According to the present invention it is further preferred that the one or more zeolitic materials having a BEA framework structure provided as a catalyst in step (a) of the inventive process display an X-ray diffraction pattern comprising at least the following reflections:

| Intensity (%) | Diffraction angle 2θ/° [Cu K(alpha 1)] |
|---|---|
| [9-29] | [21.06-21.26] |
| 100 | [22.11-22.31] |
| [10-30] | [25.01-25.21] |
| [6-26] | [25.54-25.74] |
| [8-28] | [26.77-26.97] |
| [12-32] | [28.38-28.58] |
| [27-47] | [29.22-29.42] |
| [7-27] | [29.99-30.19] |
| [9-29] | [32.85-33.25] |
| [11-31] | [42.86-43.26] | wherein more preferably the X-ray diffraction pattern comprises at least the following reflections:

| Intensity (%) | Diffraction angle 2θ/° [Cu K(alpha 1)] |
|---|---|
| [9-29] | [21.11-21.21] |
| 100 | [22.16-22.26] |
| [10-30] | [25.06-25.16] |
| [6-26] | [25.59-25.69] |
| [8-28] | [26.82-26.92] |
| [12-32] | [28.43-28.53] |
| [27-47] | [29.27-29.37] |
| [7-27] | [30.04-30.14] |
| [9-29] | [33.00-33.10] |
| [11-31] | [43.01-43.11] | wherein 100% relates to the intensity of the maximum peak in the X-ray powder diffraction pattern.

Thus, according to the present invention, it is particularly preferred that the one or more zeolitic materials provided as a catalyst in step (a) has an X-ray diffraction pattern comprising at least the following reflections:

| Intensity (%) | Diffraction angle 2θ/° [Cu K(alpha 1)] |
|---|---|
| [9-29] | [21.06-21.26] |
| 100 | [22.11-22.31] |
| [10-30] | [25.01-25.21] |
| [8-28] | [26.77-26.97] |
| [12-32] | [28.38-28.58] |
| [27-47] | [29.22-29.42] |
| [7-27] | [29.99-30.19] |
| [9-29] | [32.85-33.25] |
| [11-31] | [42.86-43.26] | wherein 100% relates to the intensity of the maximum peak in the X-ray powder diffraction pattern, wherein even more preferably the X-ray diffraction pattern further comprises the following reflection:

| Intensity (%) | Diffraction angle 2θ/° [Cu K(alpha 1)] |
|---|---|
| [6-26] | [25.54-25.74] |

According to the present invention, there is no particular restriction as to the surface area of the one or more zeolitic materials provided as a catalyst in step (a) of the inventive process provided that the one or more zeolitic materials having a BEA framework structure are suitable for catalyzing the alkylation of an aliphatic organic compound. Thus, with respect to the BET surface area of the one or more zeolitic materials determined according to DIN 66135 and preferably according to ISO 9277, by way of example these may range from 200 to 700 m²/g, wherein preferably the BET surface area is comprised in the range of from 250 to 675 m²/g, more preferably from 300 to 650 m²/g, more preferably from 350 to 625 m²/g, more preferably from 400 to 600 m²/g, and even more preferably of from 450 to 575 m²/g. According to particularly preferred embodiments, the BET surface area determined according to DIN 66135 ranges from 500 to 550 m²/g.

According to the present invention, the one or more zeolitic materials provided as a catalyst in step (a) are obtainable, and preferably obtained, according to a synthetic process for the organotemplate-free synthesis of a zeolitic material having a BEA framework structure, wherein said synthetic process comprises the steps of
  (1) preparing a mixture comprising seed crystals and one or more sources for $YO_2$; and
  (2) crystallizing the mixture;
  wherein when the BEA framework preferably comprises $X_2O_3$, the mixture according to step (1) further comprises one or more sources for $X_2O_3$.

According to said preferred synthesis for providing the one or more zeolitic materials in step (a), at no point does the mixture provided in step (1) and crystallized in step (2) contain more than an impurity of an organic structure directing agent specifically used in the synthesis of the one or more zeolitic materials having a BEA framework structure, in particular specific tetraalkylammonium salts and/or related organotemplates such as tetraethylammonium and/or dibenzylmethylammonium salts, and dibenzyl-1,4-diazabicyclo[2,2,2]octane. Such an impurity can, for example, be caused by organic structure directing agents still present in seed crystals used in the preferred synthesis. Organotemplates contained in seed crystal material may not, however, participate in the crystallization process since they are trapped within the seed crystal framework and therefore may not act structure directing agents within the meaning of the present invention.

According to the present invention, a zeolitic material having a BEA framework structure is crystallized in step (2) of the preferred synthetic method. For this purpose, $YO_2$ can be provided in step (1) in any conceivable form, provided that a zeolitic material having a BEA framework structure comprising $YO_2$ can be crystallized in step (2). Preferably, $YO_2$ is provided as such and/or as a compound which comprises $YO_2$ as a chemical moiety and/or as a compound which (partly or entirely) is chemically transformed to $YO_2$ during the inventive process. In preferred embodiments of the present invention, wherein Y stands for Si or for a combination of Si with one or more further tetravalent elements, the source for $SiO_2$ provided in step (1) can be any conceivable source. There can therefore be used, for example, all types of silica and silicates, preferably fumed silica, silica hydrosols, reactive amorphous solid silicas, silica gel, silicic acid, water glass, sodium metasilicate hydrate, sesquisilicate or disilicate, colloidal silica, pyrogenic silica, silicic acid esters, or tetraalkoxysilanes, or mixtures of at least two of these compounds.

According to preferred embodiments of the preferred synthetic method, wherein the mixture according to step (1) comprises one or more sources for $SiO_2$, said source preferably comprises one or more compounds selected from the group consisting of silica and silicates, preferably silicates, more preferably alkali metal silicates. Among the preferred alkali metal silicates, the one or more sources preferably comprise water glass, more preferably sodium and/or potassium silicate, and more preferably sodium silicate. In particularly preferred embodiments of the present invention, the source for $SiO_2$ is sodium silicate. Furthermore, in embodiments comprising silica, fumed silica is preferred.

According to preferred embodiments of the present invention, wherein the one or more zeolitic materials having a BEA framework structure comprise $X_2O_3$, one or more sources for $X_2O_3$ are provided in step (1) of the preferred synthetic method. In general, $X_2O_3$ can be provided in any conceivable form, provided that a zeolitic material having a BEA framework structure comprising $X_2O_3$ can be crystallized in step (2). Preferably, $X_2O_3$ is provided as such and/or as a compound which comprises $X_2O_3$ as a chemical moiety and/or as a compound which (partly or entirely) is chemically transformed to $X_2O_3$ during the inventive process.

According to preferred embodiments of the preferred synthetic method, wherein X stands for Al or for a combination of Al with one or more further trivalent elements, the source for $Al_2O_3$ provided in step (1) can be any conceivable source. There can be used for example any type of alumina and aluminates, aluminum salts such as, for example, alkali metal aluminates, aluminum alcoholates, such as, for example, aluminum triisopropylate, or hydrated alumina such as, for example, alumina trihydrate, or mixtures thereof. Preferably, the source for $Al_2O_3$ comprises one or more compounds selected from the group consisting of alumina and aluminates, preferably aluminates, more preferably alkali metal aluminates. Among the preferred alkali metal aluminates, the one or more sources preferably comprises sodium and/or potassium aluminate, more preferably sodium aluminate. In particularly preferred embodiments of the preferred synthetic method, the source for $Al_2O_3$ is sodium aluminate.

In cases wherein the mixture of step (1) further comprises one or more sources for $X_2O_3$ including one or more boron compounds, for example free boric acid and/or borates and/or boric esters, such as, for example, triethyl borate or trimethyl borate, can be used as starting materials.

According to the preferred synthetic method it is particularly preferred that the mixture according to step (1) comprises one or more silicates as a source for $YO_2$ and one or more aluminates as a source for $X_2O_3$, more preferably one or more alkali metal silicates and/or one or more alkali metal aluminates, and even more preferably one or more water glass compounds and/or one or more alkali metal aluminates, wherein the alkali metal of said preferred embodiments preferably comprises sodium and/or potassium, more preferably sodium, and wherein the alkali metal even more preferably is sodium.

In preferred embodiments of the preferred synthetic method wherein the mixture according to step (1) comprises one or more sources for $X_2O_3$, the $YO_2:X_2O_3$ molar ratio of the mixture can have any conceivable value, provided that a zeolitic material having a BEA framework structure comprising both $YO_2$ and $X_2O_3$ is crystallized in step (2). Generally, the molar ratio ranges from 1 to 100, preferably from 5 to 85, more preferably from 10 to 60, more preferably from 20 to 55, more preferably from 25 to 50, more preferably from 35 to 45, and particularly preferably from 38 to 42.

According to the preferred synthetic method it is further preferred that the zeolitic material obtained and/or obtainable and/or the inventive material as such according to the preferred synthetic method comprises one or more alkali metals M, preferably sodium and/or potassium, and more preferably sodium. The alkali metal can be added at any conceivable stage of the preferred synthetic method, wherein preferably it is also added in step (1). More preferably, the entire quantity of the alkali metal comprised in the zeolitic material having a BEA framework structure is added in step (1) of the preferred synthetic method. In particularly preferred embodiments of the preferred synthetic method, the alkali metal is partly or entirely contained in the one or more sources for $YO_2$ and/or $X_2O_3$ provided in step (1), wherein preferably, the alkali metal is partly provided by a further source. According to said particularly preferred embodiments wherein the one or more alkali metals M are partly provided by one or more further sources, there is no general restriction as to which type of source may be used, provided that a zeolitic material having a BEA framework structure is obtained which as such and/or after having been subject to a step of at least partly substituting the one or more alkali metals M contained therein is suitable for catalyzing the alkylation of an organic compound. Preferably, the one or more further sources for providing one or more of the one or more alkali metals comprises one or more alkali metal halides, and or one or more alkali metal hydroxides, wherein the halides are preferably selected from the group consisting of fluoride, chloride, and bromide. According to particularly preferred embodiments of the preferred synthetic method, the one or more further sources comprise one or more alkali metal hydroxides, preferably sodium and/or potassium hydroxide, and even more preferably sodium hydroxide.

In general, the alkali metal M can be contained in the mixture according to step (1) of the preferred synthetic method in any conceivable amount, provided that a zeolitic material having a BEA framework structure is crystallized in step (2). Preferably, the $M:YO_2$ molar ratio in the mixture according to step (1) ranges from 0.1 to 2, more preferably from 0.2 to 1.5, more preferably from 0.3 to 1.2, more preferably from 0.4 to 1, more preferably from 0.5 to 0.9, more preferably from 0.55 to 0.8, and more preferably from 0.6 to 0.75. According to particularly preferred embodiments of the preferred synthetic method, the $M:YO_2$ molar ratio in the mixture according to step (1) ranges from 0.65 to 0.7.

According to the preferred synthetic method it is preferred that the mixture according to step (1) comprises one or more sources for $X_2O_3$ and one or more alkali metals M. In general, any conceivable amounts of these components can be contained in the mixture provided that a zeolitic material having a BEA framework structure is crystallized in step (2). Preferably, the $YO_2:X_2O_3:M$ molar ratios in the mixture according to step (1) range from (1-100):1:(2-90), more preferably from (5-85):1:(5-70), more preferably from (10-60):1:(8-50), more preferably from (20-55):1:(13-35), more preferably from (25-50):1:(15-30), more preferably from (35-45):1:(20-29), and even more preferably from (38-42):1:(25-28).

According to the preferred synthetic method for obtaining the one or more zeolitic materials having a BEA framework structure, the mixture provided in step (1) contains one or more sources for hydroxide anions $OH^-$. In general any conceivable source for $OH^-$ can be used, wherein the one or more sources preferably comprises a metal hydroxide, more preferably a hydroxide of an alkali metal M, more preferably sodium and/or potassium hydroxide, and even more preferably sodium hydroxide.

In general the $OH^-:YO_2$ molar ratio of the mixture according to step (1) of the preferred synthetic method can have any conceivable value, provided that a zeolitic material having a BEA framework structure is crystallized in step (2). Preferably, said molar ratio is comprised in the range of from 0.1 to 1, more preferably of from 0.4 to 0.65, more preferably of from 0.43 to 0.62, more preferably from 0.57 to 0.6, and even more preferably from 0.55 to 0.61.

According to the preferred synthetic method it is further preferred that seed crystals are provided in step (1), wherein said seed crystals comprise a zeolitic material having a BEA framework structure. In general, said seed crystals can comprise any zeolitic material having a BEA framework structure, provided that a zeolitic material having a BEA framework structure is crystallized in step (2). Preferably, the zeolitic material having a BEA framework structure comprised in the seed crystals is a zeolitic material which is obtainable and preferably obtained according to the preferred synthetic method. More preferably, the zeolitic material having a BEA framework structure comprised in the seed crystals is the same as the zeolitic material having a BEA framework structure which is then crystallized in step (2). Particularly preferred are seed crystals comprising zeolite beta, more preferably zeolite beta which is obtainable or has preferably been obtained according to the preferred synthetic method. In particularly preferred embodiments, the seed crystals are zeolite beta crystals, preferably zeolite beta crystals which are obtainable or have preferably been obtained according to the preferred synthetic method.

According to the preferred synthetic method, any suitable amount of seed crystals can be provided in the mixture according to step (1), provided that a zeolitic material having a BEA framework structure is crystallized in step (2). In general, the amount of seed crystals contained in the mixture according to step (1) ranges from 0.1 to 50 wt.-% based on 100 wt.-% of $YO_2$ in the one or more sources for $YO_2$, preferably from 0.5 to 40 wt.-%, more preferably from 1 to 35 wt.-%, more preferably from 2 to 25 wt.-%, more preferably from 3 to 20 wt.-%, more preferably from 5 to 15 wt.-%, and even more preferably from 8 to 12 wt.-%.

In step (1) according to the preferred synthetic method, the mixture can be prepared by any conceivable means, wherein mixing by agitation is preferred, preferably by means of stirring.

According to the preferred synthetic method it is preferred that the mixture according to step (1) further comprises a solvent. Any conceivable solvent can be used in any conceivable amount, provided that a zeolitic material having a BEA framework structure can be crystallized in step (2) of the preferred synthetic method. Preferably, the solvent comprises water, wherein the $H_2O:YO_2$ molar ratio of the mixture ranges from 1 to 100, preferably from 2 to 60, more preferably from 5 to 50, more preferably from 7 to 45, more preferably from 10 to 30, and particularly preferably from 15 to 25. According to the preferred synthetic method, it is further preferred that the $H_2O:YO_2$ molar ratio of the mixture ranges from 15 to 45, more preferably from 20 to 40, and even more preferably from 25 to 35. In particularly preferred embodiments, the solvent provided in step (1) is distilled water.

In general, the single components for providing the mixture of step (1) of the preferred synthetic method can be added in any order, provided that a zeolitic material having a BEA framework structure is crystallized from the mixture in step (2) of the preferred synthetic method. This may, for example, involve the addition of the optional solvent and optionally the one or more sources for $X_2O_3$ and/or the one or more sources for $OH^-$, followed by the addition of the one or more sources for $YO_2$, wherein the seed crystals are only added to the mixture afterwards. Alternatively, the addition of the optional solvent and optionally the one or more sources for $X_2O_3$ and/or the one or more sources for OH may be first followed by the addition of the seed crystals, wherein the one or more sources for $YO_2$ is only added thereafter.

In general, step (2) according to the preferred synthetic method can be conducted in any conceivable manner, provided that a zeolitic material having a BEA framework structure is crystallized from the mixture according to step (1). The mixture can be crystallized in any type of vessel, wherein a means of agitation is optionally employed, said agitation being preferably achieved by rotation of the vessel and/or stirring, and more preferably by stirring the mixture.

According to the preferred synthetic method, the mixture is preferably heated during at least a portion of the crystallization process in step (2). In general, the mixture can be heated to any conceivable temperature of crystallization, provided that a zeolitic material having a BEA framework structure is crystallized from the mixture. Preferably, the mixture is heated to a temperature of crystallization ranging from 80 to 200° C., more preferably from 90 to 180° C., more preferably from 95 to 170° C., more preferably from 100 to 160° C., more preferably from 110 to 150° C., and even more preferably from 115 to 145° C.

The preferred heating in step (2) of the preferred synthetic method can be conducted in any conceivable manner suitable for the crystallization of a zeolitic material having a BEA framework structure. In general, heating may be conducted at one temperature of crystallization or vary between different temperatures. Preferably, a heat ramp is used for reaching the temperature of crystallization, wherein, by way of example, the heating rate may range from 10 to 100° C./h, more preferably from 20 to 70° C./h, more preferably from 25 to 60° C./h, more preferably from 30 to 50° C./h, and even more preferably from 35 to 45° C./h.

According to the preferred synthetic method it is preferred that the mixture according to step (1) is subjected in step (2) to a pressure which is elevated with regard to normal pressure. The term "normal pressure" as used in the context of the present invention relates to a pressure of 101,325 Pa in the ideal case. However, this pressure may vary within boundaries known to the person skilled in the art. By way of example, this pressure can be in the range of from 95,000 to 106,000 or of from 96,000 to 105,000 or of from 97,000 to 104,000 or of from 98,000 to 103,000 or of from 99,000 to 102,000 Pa.

In preferred embodiments of the preferred synthetic method wherein a solvent is present in the mixture according to step (1), it is furthermore preferred that heating in step (2) is conducted under solvothermal conditions, meaning that the mixture is crystallized under autogenous pressure of the solvent which is used, for example by conducting heating in an autoclave or other crystallization vessel suited for generating solvothermal conditions. In particularly preferred embodiments wherein the solvent comprises or consists of water, preferably of distilled water, heating in step (2) is accordingly preferably conducted under hydrothermal conditions.

The apparatus which can be used in the preferred synthetic method for crystallization is not particularly restricted, provided that the desired parameters for the crystallization process can be realized, in particular with respect to the preferred embodiments requiring particular crystallization conditions. In the preferred embodiments conducted under solvothermal conditions, any type of autoclave or digestion vessel can be used, wherein a Teflon-lined apparatus is preferred.

In general, the duration of the crystallization process in step (2) of the preferred synthetic method is not particularly limited. In preferred embodiments involving heating of the mixture according to step (1), said crystallization process is conducted for a period ranging from 10 to 200 h, more preferably from 30 to 150 h, more preferably from 100 to 140 h, and even more preferably from 110 to 130 h. According to the preferred synthetic method, it is further preferred that crystallization is conducted for a period ranging from 5 to 100, 10 to 80 h, more preferably from 20 to 70 h, more preferably from 30 to 60 h, more preferably from 40 to 55 h, and even more preferably from 45 to 50 h.

According to preferred embodiments of the preferred synthetic method, wherein the mixture is heated in step (2), said heating may be conducted during the entire crystallization process or during only one or more portions thereof, provided that a zeolitic material having the BEA framework structure is crystallized. Preferably, heating is conducted during the entire duration of crystallization.

In general, the process of the preferred synthetic method can optionally comprise further steps for the work-up and/or further physical and/or chemical transformation of the zeolitic material having a BEA framework structure crystallized in step (2) from the mixture provided in step (1). The crystallized material can for example be subject to any sequence of isolation and/or washing procedures, wherein the zeolitic material obtained from crystallization in step (2) is preferably subject to one or more isolation and one or more washing procedures.

Isolation of the crystallized product can be achieved by any conceivable means. Preferably, isolation of the crystallized product can be achieved by means of filtration, ultra-filtration, diafiltration, centrifugation and/or decantation methods, wherein filtration methods can involve suction and/or pressure filtration steps.

With respect to one or more optional washing procedures, any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and one or more alcohols, such as water and methanol or water and ethanol or water and propanol or water and methanol and ethanol or water and methanol and propanol or water and ethanol and propanol or water and methanol and ethanol and propanol. Water or a mixture of water and one or more alcohols, preferably water and ethanol, is preferred, distilled water being very particularly preferred as the only washing agent.

Preferably, the separated zeolitic material is washed until the pH of the washing agent, preferably the washwater, is in the range of from 6 to 8, preferably from 6.5 to 7.5, as determined via a standard glass electrode.

Furthermore, the preferred synthetic method can optionally comprise one or more drying steps. In general, any conceivable means of drying can be used. Drying procedures preferably include heating and/or applying vacuum to the zeolitic material having a BEA framework structure. In envisaged embodiments of the preferred synthetic method, one or more drying steps may involve spray drying, preferably spray granulation of the zeolitic material.

In embodiments which comprise one or more drying steps, the drying temperatures are preferably in the range of from 25° C. to 150° C., more preferably of from 60 to 140° C., more preferably of from 70 to 130° C. and even more preferably in the range of from 75 to 125° C. The durations of drying are preferably in the range of from 2 to 60 h, more preferably in the range of from 6 to 48 hours, and even more preferably of from 12 to 24 h.

According to the preferred synthetic method, the zeolitic material crystallized in step (2) is preferably subject to one or more ion-exchange procedures. In general, any conceivable ion-exchange procedure with all possible ionic elements and/or molecules can be conducted on the zeolitic material. Preferably, as ionic elements one or more cation and/or cationic elements are employed which preferably comprise one or more cations and/or cationic elements selected from $H^+$ and $NH_4^+$, wherein more preferably the one or more cation and/or cationic elements are $H^+$ and/or $NH_4^+$, preferably $H^+$. According to the preferred synthetic method, it is particularly preferred that the zeolitic material crystallized in step (2) is first ion-exchanged with $NH_4^+$ and subsequently calcined for transforming the ammonium cations into H+, and thus obtaining the H-form of the zeolitic material crystallized in step (2).

In general, the optional washing and/or isolation and/or ion-exchange procedures comprised in the preferred synthetic method can be conducted in any conceivably order and repeated as often as desired.

Therefore, the preferred synthetic method optionally comprises one or more of the following steps of
  (3) isolating the zeolitic material having a BEA framework structure, preferably by filtration, and/or
  (4) washing the zeolitic material having a BEA framework structure, and/or
  (5) drying the zeolitic material having a BEA framework structure, and/or
  (6) subjecting the zeolitic material having a BEA framework structure to an ion-exchange procedure,
  wherein the steps (3) and/or (4) and/or (5) and/or (6) can be conducted in any order, and wherein one or more of said steps is preferably repeated at least once.

Preferably, the preferred synthetic method comprises one or more steps of isolating the zeolitic material crystallized according to step (2), more preferably by filtration thereof. According to the preferred synthetic method it is further preferred that after the one or more steps of isolating, the zeolitic material is subject to one or more steps of drying, wherein more preferably the zeolitic material is subject to one or more steps of washing prior to the one or more drying steps. In a particularly preferred embodiment, the zeolitic material crystallized according to step (2) is subject to one or more steps of isolating, followed by one or more steps of washing, followed by one or more steps of drying.

According to the preferred synthetic method it is further preferred that the zeolitic material crystallized in step (2) is directly subject to one or more steps of drying, preferably to spray drying and or spray granulation, without isolating, washing, or drying of the zeolitic material beforehand. Directly subjecting the mixture obtained from step (2) of the preferred synthetic method to a spray drying or spray granulation stage has the advantage that isolation and drying is performed in a single stage.

According to the preferred synthetic method it is further preferred that the zeolitic material obtained from crystallization in step (2) is subject to one or more isolating steps prior to being subject to one or more ion-exchange procedures, preferably to one or more isolating steps followed by one or more washing steps, and more preferably to one or more isolating steps followed by one or more washing steps followed by one or more drying steps.

The preferred synthetic method preferably does not comprise a calcination step generally involving the heating of the zeolitic material crystallized according to step (2) above a temperature of 500° C. More preferably, the preferred synthetic method for the production of a zeolitic material having a BEA framework structure which does not comprise a calcination step refers to synthetic methods, wherein the zeolitic material crystallized according to step (2) is not subject to a temperature exceeding 450° C., more preferably 350° C., more preferably 300° C., more preferably 250° C., more preferably 200° C., and even more preferably 150° C. According to the preferred synthetic method it is particularly preferred that after completion of step (2) of the preferred synthetic method, wherein the crystallized zeolitic material is at ambient temperature, said material is subsequently not subject to any heating process.

Thus, according to the present invention, the one or more zeolitic materials provided as a catalyst in step (a) of the inventive process are preferably obtainable, and even more preferably obtained according to one or more of the aforementioned preferred and particularly preferred synthetic methods.

As regards the one or more aliphatic organic compounds with which the catalyst is contacted in step (b) of the inventive process, there is no particular restriction as to the type of organic compounds which may be used as the one or more aliphatic organic compounds, provided that it may be alkylated with the one or more alkylating agents employed in said step. In this respect, it is noted that within the meaning of the present invention, the one or more alkylated organic compounds obtained in step (b) comprise one or more alkylated organic compounds which are the alkylation product of the reaction of one or more aliphatic organic compounds with one or more alkylating agents. Thus, in principle, the aliphatic organic compound may be any aliphatic organic compound capable of reacting with at least one of the one or more alkylating agents used in step (b), wherein during the course of the reaction at least one covalent bond is formed between a carbon atom of the aliphatic organic compound and a carbon atom of one or more of the one or more alkylating agents. As to the type of covalent bond which is formed between the aliphatic organic compound and the alkylating agent, there is again no particular restriction. Thus, in function of the valence of the one or more carbon atoms of the aliphatic organic compound which forms a covalent bond with a carbon atom of the one or more alkylating agents, one or more single, double, and/or triple bonds may be formed, wherein preferably one or more single and/or double bonds are formed. According to the inventive process it is however even more preferred that one or more single bonds are formed between one or more carbon atoms of the aliphatic organic compound and one or more carbon atoms of the one or more alkylating agents.

According to the inventive process, the one or more aliphatic organic compounds are preferably selected from the group consisting of optionally substituted and/or optionally cyclic and and/or optionally branched (C2-C20)hydrocarbons and mixtures of two or more thereof, preferably (C2-C16)hydrocarbons, more preferably (C2-C16)hydrocarbons, more preferably (C2-C14)hydrocarbons, more preferably (C2-C12)hydrocarbons, more preferably (C2-C10)hydrocarbons, more preferably (C2-C8)hydrocarbons, more preferably (C2-C6)hydrocarbons, more preferably (C3-C5) hydrocarbons, and more preferably C4-hydrocarbons and mixtures thereof.

It is further preferred according to the inventive process that the one or more optionally substituted and/or optionally cyclic hydrocarbons are branched, wherein preferably the one or more branched hydrocarbons have the formula

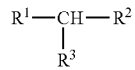

wherein independently from one another R¹, R², and R³ are optionally substituted and/or optionally cyclic and/or optionally branched (C1-C8)alkyl, preferably (C1-C6)alkyl, more preferably (C1-05)alkyl, wherein more preferably R¹, R², and R³ are, independently from one another, optionally substituted and/or optionally branched (C1-C4)alkyl, preferably (C1-C3)alkyl, wherein more preferably R¹, R², and R³ are, independently from one another, optionally substituted methyl or ethyl, preferably optionally substituted methyl. According to the present invention, it is therefore preferred that the preferred branched hydrocarbons having the formula

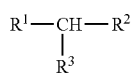

according to any of the aforementioned particular and preferred embodiments are selected from the group consisting of optionally substituted and/or optionally cyclic (C2-C20) hydrocarbons and mixtures of two or more thereof, preferably (C2-C16)hydrocarbons, more preferably (C2-C16)hydrocarbons, more preferably (C2-C14)hydrocarbons, more preferably (C2-C12)hydrocarbons, more preferably (C2-C10)hydrocarbons, more preferably (C2-C8)hydrocarbons, more preferably (C2-C6)hydrocarbons, more preferably (C3-C5)hydrocarbons, and more preferably C4-hydrocarbons and mixtures thereof.

As regards functional groups with which the one or more aliphatic organic compounds may be substituted, no particular restrictions apply such that in principle the one or more aliphatic organic compounds may be substituted with any suitable functional groups. Thus, by way of example, the one or more aliphatic compounds may be substituted with one or more functional groups selected from the group consisting of hydroxyl, halogen, carbonyl, aldehyde, carbonate ester, carboxylate, carboxyl, ester, ether, carboxamide, amine, imine, cyanate, isocyanate, nitrate, nitrile, isonitrile, sulfide, sulfinyl, sulfonyl, sulfino, sulfo, thiocyanate, isothiocyanate, phosphino, phosphono, and phosphate. It is, however, preferred according to the present invention that the one or more functional groups with which the one or more aliphatic organic compounds may be substituted are selected from the group consisting of hydroxyl, halogen, carbonyl, aldehyde, carboxylate, carboxyl, ester, ether, carboxamide, amine, imine, cyanate, isocyanate, nitrate, nitrile, isonitrile, and combinations of two or more thereof, more preferably from the group consisting of hydroxyl, halogen, carbonyl, aldehyde, carboxylate, carboxyl, ester, ether, and combinations of two or more thereof, more preferably from the group consisting of hydroxyl, halogen, carbonyl, alkoxy, and combinations of two or more thereof, more preferably from the group consisting of hydroxyl, fluoro, chloro, bromo, (C1-C3)alkoxy, and combinations of two or more thereof, more preferably from the group consisting of hydroxyl, fluoro, chloro, (C1-C2)alkoxy, and combinations of two or more thereof, and more preferably from the group consisting of hydroxyl, fluoro, chloro, methoxy, and combinations of two or more thereof. According to the present invention it is particularly preferred that the one or more functional groups with which the one or more aliphatic organic compounds may be substituted are hydroxyl.

As to the amount of functional groups with which the one or more aliphatic organic compounds according to any of the particular and preferred embodiments of the present application may be substituted, by way of example their number may range anywhere from 1 to 10, wherein preferably the preferred aliphatic organic compounds are substituted with from 1 to 5 functional groups, more preferably with from 1 to 4, more preferably with from 1 to 3, more preferably with 1 or 2, and even more preferably with 1 functional group.

It is, however, preferred according to the present invention that the one or more aliphatic organic compounds employed in the inventive process according to any of the particular and preferred embodiments of the present application are unsubstituted hydrocarbons consisting of carbon and hydrogen atoms, wherein preferably the one or more aliphatic organic compounds comprise isobutane, wherein more preferably the one or more aliphatic organic compounds are isobutane, wherein more preferably isobutane is used as the one or more aliphatic organic compounds.

With respect to the actual alkylation of the aliphatic organic compound in step (b) of the inventive process, there is no particular restriction as to the position or positions at which the one or more aliphatic organic compounds are alkylated, provided that one or more covalent bonds are formed between a carbon atom of the one or more aliphatic organic compounds and a carbon atom of one or more of the one or more alkylating agents. As concerns the one or more alkylating agents used in the inventive process, there is principally no restriction as to the type of compounds which may be used to this effect, provided that they may be suitably used to alkylate one or more of the one or more aliphatic organic compounds. Same applies accordingly with respect to the type of alkyl moiety contained in the alkylating agent such that in principle any substituted or unsubstituted cyclic, linear, or branched alkyl moiety may be contained therein, wherein the preferred and particularly preferred functional groups with which the alkyl moieties of the one or more alkylating agents may be substituted preferably comprise one or more functional groups selected among those defined in the foregoing with respect to the preferred aliphatic organic compounds. According to particularly preferred embodiments of the inventive process, the alkyl moiety is an unsubstituted and preferably linear and unbranched alkyl moiety.

Within the meaning of the present invention, the term "alkyl moiety" preferably refers to the moiety contained in the alkylating agent which is bound to one or more of the one or more aliphatic organic compounds during the alkylation reaction of the inventive process. Regarding the size of the alkyl moiety contained in the one or more alkylating agents, there is again no general restriction in this respect according to the inventive process, such that in principle any suitable alkyl moiety may be contained in the one or more alkylating agents, provided that said alkyl moiety may be covalently bound to one or more of the one or more aliphatic organic compounds during the alkylation reaction in step (b) of the inventive process. Thus, by way of example, the size of the substituted or unsubstituted cyclic, linear, and/or branched alkyl moiety may be comprised in the range of from $C_1$ to $C_{22}$, wherein preferably it is comprised in the range of from $C_1$ to $C_{20}$, more preferably in the range of from $C_1$ to $C_{18}$, more preferably of from $C_1$ to $C_{16}$, more preferably of from $C_1$ to $C_{14}$, more preferably of from $C_1$ to $C_{10}$, more preferably of from $C_1$ to $C_8$, more preferably of from $C_2$ to $C_6$, more preferably of from $C_3$ to $C_5$, wherein even more preferably the alkyl moiety is a $C_4$ alkyl moiety.

By way of example, regarding the one or more alkylating agents used in step (b) of the inventive process, one or more compounds may be comprised therein which are selected from the group consisting of olefins, alcohols, aldehydes, alkyl halides, and mixtures of two or more thereof, wherein preferably the one or more alkylating agents comprise one or more compounds selected from the group consisting of olefins, alcohols, alkyl halides, and mixtures of two or more thereof, more preferably from the group consisting of olefins, alcohols, and mixtures thereof, wherein even more preferably the one or more alkylating agents comprise one or more olefins.

Regarding preferred embodiments of the present invention wherein the one or more alkylating agents comprise one or more olefins, there is no particular restriction as to the olefins which may be used provided that one or more of the aliphatic organic compounds may be alkylated in step (b) of the inventive process. Thus, in principle, any conceivable number of double bonds may be present therein, wherein preferably 1 to 4 double bonds are contained therein, more preferably 1 to 3 double bonds, and even more preferably 1 or 2 double bonds are contained therein. According to the present invention it is particularly preferred that the one or more alkylating agents comprise one or more olefins containing one single double bond. Furthermore, regarding the size of the olefin preferably comprised among the one or more alkylating agents, there is again no particular restriction, provided that it is suitable for alkylating one or more of the one or more aliphatic organic compounds in step (b) of the inventive process. Thus, by way of example, the olefin may have anywhere from 2 to 20 carbon atoms, wherein it preferably has from 2 to 18 carbon atoms, more preferably from 2 to 16 carbon atoms, more preferably from 2 to 14 carbon atoms, more preferably from 2 to 12 carbon atoms, more preferably from 2 to 10 carbon atoms, more preferably from 2 to 8 carbon atoms, more preferably from 2 to 6 carbon atoms, and ore preferably from 3 to 5 carbon atoms, wherein even more preferably the olefins comprised in the one or more alkylating agents have 4 carbon atoms. Furthermore, there is also no particular restriction with respect to the structure of the olefin preferably comprised in the one or more alkylating agents, provided that it is suitable for alkylating one or more of the one or more aliphatic organic compounds. Thus, the olefin may be linear, cyclic, and/or branched, wherein a portion of the branched olefins and the linear olefins as such may be cyclic. According to particularly preferred embodiments, the one or more alkylating agents comprise one or more linear and unbranched olefins, wherein said olefins are preferably non-cyclic.

Therefore, it is preferred according to the present invention that the one or more alkylating agents comprise one or more olefins, wherein the one or more olefins preferably comprise one or more alkenes, more preferably one or more alkenes selected from the group consisting of optionally substituted and/or optionally cyclic and and/or optionally branched (C2-C20)alkenes and mixtures of two or more thereof, preferably (C2-C18)alkenes, more preferably (C2-C16)alkenes, more preferably (C2-C14) alkenes, more preferably (C2-C12) alkenes, more preferably (C2-C10)alkenes, more preferably (C2-C8) alkenes, more preferably (C2-C6) alkenes, more preferably (C3-C5) alkenes, and more preferably C4-alkenes and mixtures thereof. Furthermore, it is preferred according to any of said particular and preferred embodiments of the present invention that the one or more alkenes contain one to four C=C-double bonds, preferably one to three, more preferably one or two, and more preferably one C=C-double bond.

As regards the location of the one or more C=C-double bonds in any of the particular and preferred embodiments of the present invention wherein the one or more alkylating agents comprise one or more olefins, no particular restrictions apply such that these may be principally contained as terminal and/or internal C=C-double bonds in the one or more olefins. It is, however, preferred according to the present invention that the one or more olefins contain at least one terminal C=C-double bond and/or at least one internal C=C-double bond, preferably at least one terminal C=C-double bond.

Therefore, it is preferred according to the present invention that the one or more alkylating agents comprise one or more olefins, wherein the one or more olefins preferably comprise one or more alkenes, wherein the one or more alkenes contain at least one terminal C=C-double bond and/or at least one internal C=C-double bond, preferably at least one terminal C=C-double bond.

According to the present invention it is thus particularly preferred that the one or more alkylating agents comprise one or more olefins, wherein the one or more olefins preferably comprise one or more alkenes, wherein the one or more alkenes are selected from the group consisting of optionally substituted and/or optionally cyclic and/or optionally branched ethene, propene, butene, pentene, and mixtures of two or more thereof, wherein preferably the one or more alkenes comprise optionally substituted and/or optionally branched propene and/or butene, wherein more preferably the one or more alkenes comprise butene, wherein more preferably the one or more alkenes are butene, wherein more preferably butene is used as the one or more alkenes. According to the particularly preferred embodiments of the present invention wherein the one or more alkylating agents comprise butene, and preferably wherein butene is used as the alkyltating agents in step (b) of the inventive process, it is yet further preferred that butene is selected from the group consisting of but-1-ene, (2Z)-but-2-ene, (2E)-but-2-ene, 2-methylprop-1-ene, and mixtures of two or more thereof, preferably from the group consisting of but-1-ene, (2Z)-but-2-ene, (2E)-but-2-ene, and mixtures of two or more thereof, wherein more preferably butene comprises but-1-ene, wherein more preferably butene is but-1-ene.

As regards functional groups with which the one or more alkenes agents may be substituted, no particular restrictions apply such that in principle the one or more alkenes may be substituted with any suitable functional groups. Thus, by way of example, the one or more alkenes may be substituted with one or more functional groups selected from the group consisting of hydroxyl, halogen, carbonyl, aldehyde, carbonate ester, carboxylate, carboxyl, ester, ether, carboxamide, amine, imine, cyanate, isocyanate, nitrate, nitrile, isonitrile, sulfide, sulfinyl, sulfonyl, sulfino, sulfo, thiocyanate, isothiocyanate, phosphino, phosphono, and phosphate. It is, however, preferred according to the present invention that the one or more functional groups with which the one or more alkenes may be substituted are selected from the group consisting of hydroxyl, halogen, carbonyl, aldehyde, carboxylate, carboxyl, ester, ether, carboxamide, amine, imine, cyanate, isocyanate, nitrate, nitrile, isonitrile, and combinations of two or more thereof, more preferably from the group consisting of hydroxyl, halogen, carbonyl, aldehyde, carboxylate, carboxyl, ester, ether, and combinations of two or more thereof, more preferably from the group consisting of hydroxyl, halogen, carbonyl, alkoxy, and combinations of two or more thereof, more preferably from the group consisting of hydroxyl, fluoro, chloro, bromo, (C1-C3)alkoxy, and combinations of two or more thereof, more preferably from the group consisting of hydroxyl, fluoro, chloro, (C1-C2)alkoxy, and combinations of two or more thereof, and more preferably from the group consisting of hydroxyl, fluoro, chloro, methoxy, and combinations of two or more thereof. According to the present invention it is particularly preferred that the one or more functional groups with which the one or more alkenes may be substituted are hydroxyl.

As to the amount of functional groups with which the one or more alkenes according to any of the particular and preferred embodiments of the present application may be substituted, by way of example their number may range anywhere from 1 to 10, wherein preferably the preferred alkenes are substituted with from 1 to 5 functional groups, more preferably with from 1 to 4, more preferably with from 1 to 3, more preferably with 1 or 2, and even more preferably with 1 functional group.

It is, however, preferred according to the present invention that the one or more alkenes employed in the inventive process according to any of the particular and preferred embodiments of the present application are unsubstituted, wherein preferably the one or more alkylating agents consist of one or more unsubstituted alkenes.

According to certain embodiments of the present invention, the alkylating agents comprise mixtures of light olefins. According to said embodiments, there is no particular restriction as to the type and composition of such mixtures provided that one or more of the one or more aliphatic organic compounds may be suitably alkylated, wherein by way of example mixtures of ethylene, propylene, (linear and/or branched) butenes, and/or (linear and/or branched) pentenes. Such mixtures may be provided from any conceivable source wherein by way of example such mixtures may be obtained from refinery streams such as for example from fuel gas, gas plant off-gas such as off-gas containing ethylene and/or propylene, and naphtha cracker off-gas such as off-gas containing light olefins such as for example mixtures comprising ethane, ethylene, propane, propylene, isobutane, n-butane, (linear and/or branched) butene, and/or (linear and/or branched) pentanes, and refinery FCC streams comprising propane and propylene.

As concerns the compounds which are contacted in step (b) of the inventive process for the alkylation reaction, there is no particular restriction according to the present invention neither as to the choice of the one or more aliphatic organic compounds in view of the one or more alkylating agents which are used therein nor, vice versa, as to the choice of the one or more alkylating agents in view of the one or more aliphatic organic compounds which are used therein, provided that one or more of the one or more alkylating agents used therein is capable of alkylating one or more of the one or more aliphatic organic compounds in the presence of the catalyst comprising the one or more zeolitic materials. According to the inventive process, it is particularly preferred that the one or more aliphatic organic compounds comprise one or more branched hydrocarbons have the formula

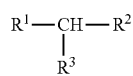

wherein independently from one another $R^1$, $R^2$, and $R^3$ are optionally substituted and/or optionally branched (C1-C4) alkyl, and the one or more alkylating agents comprise one or more alkenes selected from the group consisting of optionally substituted and/or optionally cyclic and and/or optionally branched (C2-C6) alkenes and mixtures thereof.

According to the inventive process it is further preferred that the one or more aliphatic organic compounds comprise one or more branched hydrocarbons have the formula

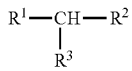

wherein independently from one another $R^1$, $R^2$, and $R^3$ are optionally substituted and/or optionally branched (C1-C3) alkyl, and the one or more alkylating agents comprise one or more alkenes selected from the group consisting of optionally substituted and/or optionally cyclic and and/or optionally branched (C3-C5) alkenes and mixtures thereof.

According the inventive process it is yet further preferred that the one or more aliphatic organic compounds comprise one or more branched hydrocarbons have the formula

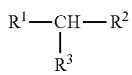

wherein $R^1$, $R^2$, and $R^3$ are, independently from one another, optionally substituted methyl or ethyl, preferably optionally substituted methyl, and the one or more alkylating agents comprise C4-alkenes and mixtures thereof.

Concerning the alkylation reaction conducted in step (b) of the inventive process, there is no particular restriction according to the present invention as to the respective amounts and proportions of the one or more aliphatic organic compounds and the one or more alkylating agents which may be used therein, nor to particular restrictions exist with respect to the reaction conditions and parameters, provided that these are suitable for allowing the reaction of one or more of the one or more aliphatic organic compounds with one or more of the one or more alkylating agents in the presence of the catalyst comprising the one or more zeolitic materials. Thus, regarding the temperatures employed in one or more of the one or more reactors in step (b), these may by way of example range anywhere from 50 to 250° C. In instances in which two or more reactors are employed in step (b), the temperatures employed in the individual reactors may be the same or may differ from one another. According to preferred embodiments, the temperature employed in one or more of the one or more reactors ranges from 60 to 200° C., more preferably from 70 to 150° C., and even more preferably from 80 to 120° C. According to particularly preferred embodiments, the temperature used in one or more of the one or more reactors ranges from 90 to 110° C.

Therefore, according to the inventive process it is preferred that step (b) is conducted at a temperature ranging from 50 to 250° C., preferably from 60 to 200° C., more preferably from 70 to 150° C., more preferably from 80 to 120° C., and even more preferably from 90 to 110° C.

Furthermore, as concerns the pressure under which the alkylation reaction in step (b) of the inventive process is conducted, there is again no particular restriction in this respect provided that the pressure which is employed in the one or more reactors is suitable for conducting alkylation. As with respect to the temperature, in instances wherein two or more reactors are employed, the pressure used in the reactors may be the same or different. Thus, by way of example, the pressure in one or more of the one or more reactors may be comprised in the range of anywhere from 1 to 50 bar, wherein preferably the pressure in one or more of the reactors is comprised in the range of from 4 to 40 bar, more preferably of from 8 to 35 bar, more preferably of from 12 to 30 bar, more preferably from 14 to 29 bar, more preferably from more preferably of from 16 to 28 bar, more preferably of from 18 to 27 bar, more preferably of from 20 to 26 bar, wherein even more preferably the pressure in one or more of the reactors is comprised in the range of from 22 to 25 bar.

Accordingly, according to the inventive process it is preferred that step (b) is conducted at a pressure comprised in the range of from 1 to 50 bar, preferably of from 4 to 40 bar, more preferably of from 8 to 35 bar, more preferably of from 12 to 30 bar, more preferably of from 14 to 29 bar, more preferably of from 16 to 28 bar, more preferably of from 18 to 27 bar, more preferably of from 20 to 26 bar, and even more preferably of from 22 to 25 bar.

According to the inventive process, the alkylation reaction is generally conducted such that the organic reactants, i.e., the one or more aliphatic organic compounds and the one or more alkylating agents, are brought into contact with an alkylation catalyst in a suitable reaction zone such in one or more of the respective one or more reactors. In this respect, there is no general restriction as to the reaction mode provided that it is suitable for obtaining one or more alkylated compounds. Accordingly, the inventive process may principally be conducted as a batch reaction, or as a continuous process, or as a combination of batch reaction and continuous process, wherein preferably it is conducted as a continuous process.

Therefore, it is preferred according to the present invention that the alkylation process is conducted in a batch or continuous mode, preferably in a continuous mode.

According to preferred embodiments of the present invention wherein the inventive process is conducted as a batch reaction, in addition to any preferred and particularly preferred reaction parameters outlined in the foregoing and below, there is no particular limitation as to the reaction time which is employed provided that one or more alkylated organic compounds may be obtained in step (b). Thus, by way of example, the duration of the batch reaction may be comprised in the range of from 0.5 to 100 h, wherein preferably the batch reaction is conducted for a duration ranging from 1 to 80 h, more preferably from 4 to 50 h, more preferably from 8 to 35 h, more preferably from 12 to 30 h, more preferably from 15 to 26 h, and even more preferably from 18 to 22 h.

Therefore, according to the present invention, and preferably according to further preferred embodiments wherein the inventive process is conducted as a batch reaction, it is preferred that step (b) is conducted for a duration of from 0.5 to 100 h, preferably of from 1 to 80 h, more preferably of from 4 to 50 h, more preferably of from 8 to 35 h, more preferably of from 12 to 30 h, more preferably of from 15 to 26 h, and even more preferably of from 18 to 22 h.

According to the present invention, it is alternatively preferred that the inventive process is conducted in a continuous mode. According to said further preferred embodiments there is no particular restriction as to the state of the catalyst comprising the one or more zeolitic materials, such that by way of example a fixed bed or a fluidized bed technology may be employed, in addition to a combination of fixed and fluidized bed technologies, wherein in instances in which both fixed and fluidized bed technologies are employed, two or more reactors are preferably employed in step (b), wherein the fixed and fluidized bed technologies are preferably confined to separate reactors, respectively. According to particularly preferred embodiments employing a continuous mode, it is however preferred that in one or more of the one or more reactors the catalyst of the inventive process is maintained as a fixed bed.

Furthermore, according to further preferred embodiments of the present invention wherein the inventive process is conducted as a continuous reaction, in addition to any preferred and particularly preferred reaction parameters outlined in the foregoing and below, there is no particular limitation as to the feed weight hourly space velocity (WHSV) which is employed in one or more of the one or more reactors used in the continuous process, provided that one or more alkylated organic compounds may be obtained in step (b). Thus, by way of example, the WHSV employed in one or more of the one or more reactors may be comprised anywhere in the range of from 0.1 to 500 $h^{-1}$, wherein the WHSV is preferably comprised in the range of from 0.5 and 100 $h^{-1}$, more preferably of from 0.1 to 20 $h^{-1}$, and even more preferably of from 1 to 6 $h^{-1}$.

Thus, according to the present invention, it is preferred that step (b) of the inventive process is carried out as a continuous process.

Furthermore, according to the present invention it is yet further preferred that the one or more reactors employed in step (b) contain the catalyst in the form of a fixed bed and/or as a fluidized bed, wherein preferably one or more of the one or more reactors contain the catalyst in the form of a fixed bed.

Thus, various types of reactors may be used in the inventive process. For example, the process may be carried out in batchwise fashion by adding the catalyst and aliphatic organic compound feedstock to a stirred autoclave, heating to a suitable reaction temperature, and then adding alkylating agent feedstock. A heat transfer fluid may be circulated through the jacket of the autoclave, or a condenser may be provided, to remove the heat of reaction and maintain a constant temperature. The process also may be performed in a catalytic distillation mode.

Further by way of example, for large scale industrial processes a fixed bed reactor operating in an upflow or downflow mode or a moving bed reactor operating with concurrent or countercurrent catalyst and hydrocarbon flows may be employed. These reactors may contain a single catalyst bed or multiple catalyst beds and may be equipped for the interstage addition of the one or more alkylating agents as well as interstage cooling. Interstage addition of the one or more alkylating agents and/or isothermal operation may be used to enhance product quality and catalyst life. Furthermore, a moving bed reactor may be used for enabling continuous removal of spent catalyst for regeneration and replacement by fresh or regenerated catalysts.

As concerns the proportions in which the one or more aliphatic organic compounds and the one or more alkylating agents are used, there is no particular limitation according to the present invention provided that one or more alkylated organic compounds are obtained in step (b). According to the inventive process it is preferred that at least an equimolar amount of the one or more aliphatic organic compounds and the one or more alkylating agents is employed, wherein preferably a molar excess of the one or more aliphatic organic compounds is used relative to the amount of the one or more alkylating agents. Thus by way of example, it is preferred according to the inventive process that the molar ratio of the one or more aliphatic organic compounds to the one or more alkylating agents is comprised in the range of from 10 to 250, and preferably of from 20 to 150. According to particularly preferred embodiments, the molar ratio is comprised in the range of from 30 to 100, more preferably of from 35 to 80, more preferably of from 40 to 60, and even more preferably of from 45 to 55.

Therefore, it is preferred according to the present invention that the molar ratio of the one or more aliphatic organic compounds to the one or more alkylating agents employed in step (b) ranges from 10 to 250, preferably from 20 to 150, more preferably from 30 to 100, more preferably from 35 to 80, more preferably from 40 to 60, and even more preferably from 45 to 55.

According to the present invention the catalyst provided in step (a) may in principle be used in any suitable form, provided that it is capable of catalyzing the alkylation reaction. Thus, the alkylation catalyst provided in step (a) which comprises one or more zeolitic materials having a BEA framework structure can be employed as such, such as by way of example in the form of a powder, a spray powder or a spray granulate.

When the inventive process is employed on an industrial scale, it is however preferable not to employ the alkylation catalyst comprising the zeolitic material as powder or sprayed material but rather in the form of a molding.

Therefore, according to the inventive process it is preferred that the catalyst comprising one or more zeolitic materials having a BEA framework structure is provided in the form of a molding.

In general, the powder or sprayed material can be shaped to form a molding without any other compounds, such as for example by suitable compacting, to obtain moldings of a desired geometry, such as in the form of tablets, cylinders, and/or spheres. The molding may however comprise all conceivable further compounds in addition to the one or more zeolitic materials comprised in the catalyst, provided that it is ensured that the resulting molding is capable of catalyzing the alkylation reaction in step (b). According to said preferred embodiments, it is further preferred that at least one suitable binder material is used in the production of the molding. In the context of this preferred embodiment, more preferably a mixture of the catalyst comprising one or more zeolitic materials and the one or more binders is prepared. Suitable binders are in general all compounds which impart adhesion and/or cohesion between the one or more zeolitic materials which are to be bound, in particular beyond the physisorption which may be present without a binder. Examples of such binders are metal oxides, such as $SiO_2$, $Al_2O_3$, $TiO_2$, $ZrO_2$ or MgO, or clays or mixtures of two or more of these compounds. As $Al_2O_3$ binders, clay minerals and naturally occurring or synthetic aluminas, for example alpha-, beta-, gamma-, delta-, eta-, kappa-, chi- or theta-alumina and the inorganic or organometallic precursor compounds thereof, such as gibbsite, bayerite, boehmite, pseudoboehmite or trialkoxyaluminates, such as aluminum triisopropylate are preferred in particular. Further preferred binders are amphiphilic compounds having a polar and a nonpolar moiety, and graphite. Further binders are, for example, clays, such as montmorillonites, kaolins, bentonites, halloysites, dickites, nacrites or anaxites.

According to the present invention, the binders can be used as such for the production of a molding. In the context of the present invention, it is however also possible to use compounds from which the binder is formed in at least one further step in the production of the moldings. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention, binders which either completely or partly consist of $SiO_2$ or are a precursor of $SiO_2$, from which $SiO_2$ is formed in at least one further step in the production of the moldings are to be mentioned. In this context, both colloidal silica and "wet process" silica as well as "dry process" silica can be used. These are very particularly preferably amorphous silica, the size of the silica particles being, for example, in the range of from 5 to 100 nm and the surface of the silica particles being in the range of from 50 to 500 $m^2/g$. Colloidal silica, preferably in the form of an alkaline and/or ammoniacal solution, more preferably in the form of an ammoniacal solution, is, for example, commercially available as, inter alia, Ludox®, Syton®, Nalco® or Snowtex®. "Wet process" silica is, for example, commercially available, inter alia, as Hi-Sil®, Ultrasil®, Vulcasil®, Santocel®, Valron-Estersil®, Tokusil® or Nipsil®. "Dry process" silica is, for example, commercially available, inter alia, as Aerosil®, Reolosil®, Cab-O-Sil®, Fransil® or ArcSilica®. The binders are preferably used in an amount which leads to the finally resulting moldings whose binder content is up to 80% by weight, more preferably in the range of from 5 to 80% by weight, more preferably in the range of from 10 to 70% by weight, more preferably in the range of from 10 to 60% by weight, more preferably in the range of from 15 to 50% by weight, more preferably in the range of from 15 to 45% by weight, particularly preferably in the range of from 15 to 40% by weight, based in each case on the total weight of the finally resulting molding.

In principle, the molding comprising the alkylation catalyst of the present invention may be obtained according to any suitable procedure, provided that the molding may catalyze the alkylation in step (b) of the inventive process. According to preferred embodiments of the present invention, the molding is obtainable and preferably obtained according to a process for the production of a molding comprising the steps of
 (I) preparing of a mixture containing the alkylation catalyst comprising the one or more zeolitic materials, and optionally at least one binder;
 (II) optionally kneading of the mixture;
 (III) molding of the kneaded mixture to give at least one molding;
 (IV) optionally drying of the at least one molding; and/or
 (V) optionally calcining of the at least one dried molding.

The term "finally resulting molding" as used in the context of the present invention relates to a molding as obtainable and preferably obtained from the optional drying and/or calcining steps (IV) and/or (V), particularly preferably as obtainable and preferably obtained from step (IV).

Therefore, the mixture of binder or precursor of a binder and the catalyst comprising one or more zeolitic materials can be mixed with at least one further compound for further processing and for the formation of a plastic material. Here, inter alia, pore formers may preferably be mentioned. In the process of the present invention, all compounds which, with regard to the finished molding, provide a certain pore size and/or a certain pore size distribution and/or certain pore volumes can be used as pore formers. Preferably used pore formers in the process of the present invention are polymers which are dispersible, suspendable or emulsifiable in water or in aqueous solvent mixtures. Preferred polymers here are polymeric vinyl compounds, for example polyalkylene oxides, such as polyethylene oxides, polystyrene, polyacrylates, polymethacrylates, polyolefins, polyamides and polyesters, carbohydrates, such as cellulose or cellulose derivatives, for example methylcellulose, or sugars or natural fibers. Further suitable pore formers are, for example, pulp or graphite. If pore formers are used in the preparation of the mixture according to (I), the pore former content, preferably the polymer content of the mixture according to (I) is preferably in the range of from 5 to 90% by weight, preferably in the range of from 15 to 75% by weight, and particularly preferably in the range of from 25 to 55% by weight, based in each case on the amount of the one or more zeolitic materials in the mixture according to (I). If desired for the pore size distribution to be achieved, a mixture of two or more pore formers may also be used. In a preferred embodiment of the process of the present invention, the pore formers are removed in a step (V) by calcination to give the porous molding. According to the present invention, however, it is particularly preferred that the molding obtained in step (III) is subsequently not subject to a calcination step. With respect to the calcination of the molding preferably used in the inventive process, the term "calcination" refers to a calcination step as defined in the foregoing with respect to the one or more zeolitic materials. Therefore, according to particularly preferred embodiments of the present invention wherein the molding obtained in step (III) is subsequently not subject to a calcination step, it is accordingly preferred according to said embodiments either not to employ a pore former or, alternatively, to use one or more pore formers which may be suitably removed either by a heating step which is not a calcination step within the meaning of the present invention and/or which may be removed by other means than by suitable heating of the preferred molding containing one or more pore formers.

In the context of a likewise preferred embodiment of the present invention, at least one pasting agent is added in the preparation of the mixture according to (I). Pasting agents which may be used are all compounds suitable for this purpose. These are preferably organic, in particular hydrophilic polymers, for example cellulose, cellulose derivatives, such as methylcellulose, starch, such as potato starch, wallpaper paste, polyacrylates, polymethacrylates, polyvinyl alcohol, polyvinylpyrrolidone, polyisobutene or polytetrahydrofuran. Accordingly, particular compounds which also act as pore formers can be used as pasting agents. In a particularly preferred embodiment of the process of the present invention as described below, these pasting agents are removed in a step (V) by calcination to give the porous molding. According to the present invention, however, it is particularly preferred that the molding obtained in step (III) is subsequently not subject to a calcination step. Therefore, according to particularly preferred embodiments of the present invention wherein the molding obtained in step (III) is subsequently not subject to a calcination step, it is accordingly preferred according to said embodiments either not to employ a pasting agent or, alternatively, to use one or more pasting agents which may be suitably removed either by a heating step which is not a calcination step within the meaning of the present invention and/or which may be removed by other means than by suitable heating of the preferred molding containing one or more pasting agents.

According to a further embodiment of the present invention, at least one acidic additive may added during the preparation of the mixture according to (I). In this respect organic acidic compounds are preferred which can be removed in an optional calcination step (V). Carboxylic acids, for example formic acid, oxalic acid and/or citric acid, are particularly preferred. It is also possible to use two or more of these acidic compounds. As for the aforementioned pore formers and pasting agents, however, it is preferred to use one or more acidic additives and preferably one or more organic acidic compounds which may be removed either by a heating step which is not a calcination step within the meaning of the present invention and/or which may be removed by other means than by suitable heating of the preferred molding containing one or more acidic additives, preferably one or more organic acidic compounds.

The order of addition of the components of the mixture according to (I) which contains the alkylation catalyst comprising the one or more zeolitic materials having a BEA framework structure is not critical. In particular is both possible first to add the at least one binder, then the at least one pore former and the at least one acidic compound and finally the at least one pasting agent and to interchange the sequence with regard to the at least one binder, the at least one pore former, the at least one acidic compound and the at least one pasting agent.

After the addition of the binder to the alkylation catalyst comprising the zeolitic materials to which, if appropriate, at least one of the compounds described above have already been added, the mixture according to (I) is normally homogenized for from 10 to 180 minutes. Inter alia, kneaders, edge mills or extruders are particularly preferably used for the homogenization. The mixture is preferably kneaded. On the industrial scale, treatment in an edge mill is preferably employed for the homogenization. The homogenization is carried out as a rule at temperatures in the range of from about 10° C. to the boiling point of the pasting agent and normal pressure or slightly superatmospheric pressure. Thereafter, if appropriate, at least one of the compounds described above can be added. The mixture thus obtained is homogenized, preferably kneaded, until an extrudable plastic material has formed.

According to the preferred process of the present invention for the production of a molding, the homogenized mixture is subsequently molded. In the context of the present invention, those processes in which the molding is effected by extrusion in conventional extruders, for example to give extrudates having a diameter of preferably from 1 to 10 mm, particularly preferably from 2 to 5 mm, are preferred for the shaping processes.

Such extrusion apparatuses are described, for example, in Ullmann's Enzyklopädie der Technischen Chemie, 4th Edition, Vol. 2, page 295 et seq., 1972. In addition to the use of a screw-type extruder, a plunger-type extruder is also preferably used for the molding. In principle, however, all known and/or suitable kneading and molding apparatuses and processes may be used for the shaping. Examples of these are inter alia: briquetting, i.e. mechanical compression with or without addition of additional binder material; pelleting, i.e. compacting by circular and/or rotational movements; sintering, i.e. the material to be molded is subjected to a thermal treatment. The shape of the moldings produced according to the invention can be chosen as desired. In particular, inter alia spheres, oval shapes, cylinders or tablets are possible.

In the context of the present invention, step (III) is preferably followed by at least one drying step. In principle, any suitable drying step may be used, provided that a dry molding is provided. According to the present invention it is however preferred that the drying step does not involve temperatures used in a calcination step within the meaning of the present invention.

In the context of the present invention, an optional drying step (IV) is optionally followed by at least one calcination step (V). According to certain embodiments, a calcination step (V) is directly carried out after the molding step (III). According to the present invention it is however preferred that the preferred molding containing the alkylation catalyst comprising the one or more zeolitic materials having the BEA framework structure is not subject to a calcination step (V) subsequently to the optional drying step (IV), wherein according to said particularly preferred embodiments not involving a calcination step (V) it is preferred that the production process comprises one or more drying steps (IV) subsequently to the molding step (III).

According to embodiments wherein the preferred molding is obtainable and preferably obtained according to the aforementioned preferred method for the production of a molding which comprises one or more calcination steps (V), the calcination may be generally carried out at any temperature as defined within the meaning of the present invention, wherein it is preferably carried out at temperatures in the range of from 300 to 700° C., and more preferably from 400 to 600° C. According to said embodiments, the calcination can be effected under any suitable gas atmosphere, air and/or lean air being preferred. Furthermore, the calcination is preferably carried out in a muffle furnace, a rotary kiln and/or a belt calcination oven. It is possible for the temperatures during a calcination step to remain constant or to be changed continuously or discontinuously. If calcination is effected twice or more often, the calcination temperatures can be different or identical in the individual steps.

Before and/or after the optional drying step (IV) and/or before and/or after the optional calcination step (V), the at least one molding can, if appropriate, be treated with a concentrated or dilute Broenstedt acid or a mixture of two or more Broenstedt acids. Suitable acids are, for example, hydrochloric acid, sulfuric acid, phosphoric acid, nitric acid or carboxylic acids, dicarboxylic acids or oligo- or polycarboxylic acids, such as nitrilotriacetic acid, sulfosalicylic acid or ethylenediaminetetraacetic acid. If appropriate, this at least one treatment with at least one Broenstedt acid is followed by at least one drying step (IV) and/or at least one calcination step (V).

According to a further embodiment of the process of the present invention, the moldings preferably provided in step (a) and used in step (b) can, for better hardening, be subject to a water steam treatment, after which preferably drying is effected at least once again and/or calcination is effected at least once again. For example, after at least one drying step and at least one subsequent calcination step, the calcined molding is subjected to the steam treatment and is then dried at least once again and/or calcined at least once again.

The present invention is further illustrated by the following set of embodiments and combinations of embodiments resulting from the dependencies and back-references as indicated. In particular, it is noted that in each instance where a range of embodiments is mentioned, for example in the context of a term such as "The process of any one of embodiments 1 to 4", every embodiment in this range is meant to be explicitly disclosed for the skilled person, i.e. the wording of this term is to be understood by the skilled person as being synonymous to "The process of any one of embodiments 1, 2, 3, and 4".

1. A process for the alkylation of an aliphatic organic compound comprising:
    (a) providing a catalyst comprising one or more zeolitic materials having a BEA framework structure, wherein the BEA framework structure comprises $YO_2$ and optionally comprises $X_2O_3$, wherein Y is a tetravalent element, and X is a trivalent element,
    (b) contacting the catalyst with one or more aliphatic organic compounds in the presence of one or more alkylating agents in one or more reactors for obtaining one or more alkylated organic compounds, wherein the one or more zeolitic materials are obtainable from a synthetic process which does not employ an organotemplate as structure directing agent.
2. The process of embodiment 1, wherein one or more zeolitic materials are non-calcined.
3. The process of embodiment 1 or 2, wherein Y is selected from the group consisting of Si, Sn, Ti, Zr, Ge, and combinations of two or more thereof, Y preferably being Si.
4. The process of any of embodiments 1 to 3, wherein X is selected from the group consisting of Al, B, In, Ga, and combinations of two or more thereof, X preferably being Al.
5. The process of any of embodiments 1 to 4, wherein the Y:X molar ratio of one or more of the one or more zeolitic materials is in the range of from 1 to 100, preferably of from 2 to 50, more preferably of from 2.5 to 30, more preferably of from 3 to 20, more preferably of from 3.5 to 15, more preferably of from 3.7 to 10, more preferably of from 3.9 to 8, more preferably of from 4.1 to 6, more preferably of from 4.3 to 5.5, and more preferably in the range of from 4.5 to 5.
6. The process of any of embodiments 1 to 5, wherein the one or more zeolitic materials contain $H^+$ as counterions to the framework of the one or more zeolitic materials, wherein preferably, besides $H^+$ contained as counterions in the one or more zeolitic materials, the one or more zeolitic materials contain 5 wt.-% or less of non-framework elements based on 100 wt.-% of $YO_2$, preferably 3 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, and more preferably 0.001 wt.-% or less of non-framework elements based on 100 wt.-% of $YO_2$.
7. The process of embodiment 6, wherein the non-framework elements are Na and/or K as non-framework elements, preferably Li, Na, and K as non-framework elements, more preferably alkali metals as non-framework elements, more preferably alkali and alkaline earth metals as non-framework elements, more preferably alkali, alkaline earth, and transition metals as non-framework elements, and more preferably metals as non-framework elements.
8. The process of any of embodiments 1 to 7, wherein one or more of the one or more zeolitic materials have an X-ray diffraction pattern comprising at least the following reflections:

| Intensity (%) | Diffraction angle 2θ/° [Cu K(alpha 1)] |
|---|---|
| [9-29] | [21.06-21.26] |
| 100 | [22.11-22.31] |
| [10-30] | [25.01-25.21] |
| [8-28] | [26.77-26.97] |
| [12-32] | [28.38-28.58] |

-continued

| Intensity (%) | Diffraction angle 2θ/° [Cu K(alpha 1)] |
|---|---|
| [27-47] | [29.22-29.42] |
| [7-27] | [29.99-30.19] |
| [9-29] | [32.85-33.25] |
| [11-31] | [42.86-43.26] | wherein 100% relates to the intensity of the maximum peak in the X-ray powder diffraction pattern.

9. The process of embodiment 8, wherein the X-ray diffraction pattern further comprises the following reflection:

| Intensity (%) | Diffraction angle 2θ/° [Cu K(alpha 1)] |
|---|---|
| [6-26] | [25.54-25.74] |

10. The process of any of embodiments 1 to 9, wherein the BET surface area determined according to ISO 9277 of one or more of the one or more zeolitic materials ranges from 200 to 700 m²/g, preferably from 250 to 675 m²/g, more preferably from 300 to 650 m²/g, more preferably from 350 to 625 m²/g, more preferably from 400 to 600 m²/g, more preferably from 450 to 575 m²/g, and even more preferably from 500 to 550 m²/g.

11. The process of any of embodiments 1 to 10, wherein the one or more zeolitic materials comprise zeolite beta, preferably wherein the one or more zeolitic materials are zeolite beta, wherein more preferably zeolite beta is used as the one or more zeolitic materials.

12. The process of any of embodiments 1 to 11, wherein the one or more aliphatic organic compounds are selected from the group consisting of optionally substituted and/or optionally cyclic and and/or optionally branched (C2-C20)hydrocarbons and mixtures of two or more thereof, preferably (C2-C16)hydrocarbons, more preferably (C2-C16)hydrocarbons, more preferably (C2-C14)hydrocarbons, more preferably (C2-C12)hydrocarbons, more preferably (C2-C10)hydrocarbons, more preferably (C2-C8)hydrocarbons, more preferably (C2-C6)hydrocarbons, more preferably (C3-C5)hydrocarbons, and more preferably C4-hydrocarbons and mixtures thereof.

13. The process of embodiment 12, wherein the one or more optionally substituted and/or optionally cyclic hydrocarbons are branched, wherein preferably the one or more branched hydrocarbons have the formula

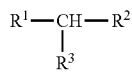

wherein independently from one another $R^1$, $R^2$, and $R^3$ are optionally substituted and/or optionally cyclic and/or optionally branched (C1-C8)alkyl, preferably (C1-C6)alkyl, more preferably (C1-C5)alkyl, wherein more preferably $R^1$, $R^2$, and $R^3$ are, independently from one another, optionally substituted and/or optionally branched (C1-C4)alkyl, preferably (C1-C3)alkyl, wherein more preferably $R^1$, $R^2$, and $R^3$ are, independently from one another, optionally substituted methyl or ethyl, preferably optionally substituted methyl.

14. The process of embodiment 12 or 13, wherein the one or more aliphatic organic compounds are substituted with one or more functional groups, wherein the one or more functional groups are preferably selected from the group consisting of hydroxyl, halogen, carbonyl, aldehyde, carbonate ester, carboxylate, carboxyl, ester, ether, carboxamide, amine, imine, cyanate, isocyanate, nitrate, nitrile, isonitrile, sulfide, sulfinyl, sulfonyl, sulfino, sulfo, thiocyanate, isothiocyanate, phosphino, phosphono, and phosphate,
more preferably from the group consisting of hydroxyl, halogen, carbonyl, aldehyde, carboxylate, carboxyl, ester, ether, carboxamide, amine, imine, cyanate, isocyanate, nitrate, nitrile, isonitrile, and combinations of two or more thereof,
more preferably from the group consisting of hydroxyl, halogen, carbonyl, aldehyde, carboxylate, carboxyl, ester, ether, and combinations of two or more thereof, more preferably from the group consisting of hydroxyl, halogen, carbonyl, alkoxy, and combinations of two or more thereof,
more preferably from the group consisting of hydroxyl, fluoro, chloro, bromo, (C1-C3)alkoxy, and combinations of two or more thereof,
more preferably from the group consisting of hydroxyl, fluoro, chloro, (C1-C2)alkoxy, and combinations of two or more thereof,
more preferably from the group consisting of hydroxyl, fluoro, chloro, methoxy, and combinations of two or more thereof,
wherein more preferably the one or more aliphatic compounds are substituted with one or more hydroxyl groups.

15. The process of embodiment 12 or 13, wherein the one or more aliphatic organic compounds are unsubstituted hydrocarbons, wherein preferably the one or more aliphatic organic compounds comprise isobutane, wherein more preferably the one or more aliphatic organic compounds are isobutane, wherein more preferably isobutane is used as the one or more aliphatic organic compounds.

16. The process of any of embodiments 1 to 15, wherein the one or more alkylating agents comprise one or more compounds selected from the group consisting of olefins, alcohols, aldehydes, alkyl halides, and mixtures of two or more thereof, preferably from the group consisting of olefins, alcohols, alkyl halides, and mixtures of two or more thereof, more preferably from the group consisting of olefins, alcohols, and mixtures thereof, wherein even more preferably the one or more alkylating agents comprise one or more olefins.

17. The process of embodiment 16, wherein the olefins comprise one or more alkenes, more preferably one or more alkenes selected from the group consisting of optionally substituted and/or optionally cyclic and and/or optionally branched (C2-C20)alkenes and mixtures of two or more thereof, preferably (C2-C18)alkenes, more preferably (C2-C16)alkenes, more preferably (C2-C14) alkenes, more preferably (C2-C12) alkenes, more preferably (C2-C10)alkenes, more preferably (C2-C8) alkenes, more preferably (C2-C6) alkenes, more preferably (C3-C5) alkenes, and more preferably C4-alkenes and mixtures thereof.

18. The process of embodiment 17, wherein the one or more alkenes contain one to four C=C-double bonds, preferably one to three, more preferably one or two, and more preferably one C=C-double bond.

19. The process of any of embodiments 17 to 18, wherein the one or more alkenes contain at least one terminal C=C-double bond and/or at least one internal C=C-double bond, preferably at least one terminal C=C-double bond.

20. The process of any of embodiments 17 to 19, wherein the one or more alkenes are selected from the group consisting of optionally substituted and/or optionally cyclic and/or optionally branched ethene, propene, butene, pentene, and mixtures of two or more thereof, wherein preferably the one or more alkenes comprise optionally substituted and/or optionally branched propene and/or butene, wherein more preferably the one or more alkenes comprise butene, wherein more preferably the one or more alkenes are butene, wherein more preferably butene is used as the one or more alkenes.

21. The process of embodiment 20, wherein butene is selected from the group consisting of but-1-ene, (2Z)-but-2-ene, (2E)-but-2-ene, 2-methylprop-1-ene, and mixtures of two or more thereof, preferably from the group consisting of but-1-ene, (2Z)-but-2-ene, (2E)-but-2-ene, and mixtures of two or more thereof, wherein more preferably butene comprises but-1-ene, wherein more preferably butene is but-1-ene.

22. The process of any of embodiments 17 to 21, wherein the one or more alkenes agents are substituted with one or more functional groups, wherein the one or more functional groups are preferably selected from the group consisting of hydroxyl, halogen, carbonyl, aldehyde, carbonate ester, carboxylate, carboxyl, ester, ether, carboxamide, amine, imine, cyanate, isocyanate, nitrate, nitrile, isonitrile, sulfide, sulfinyl, sulfonyl, sulfino, sulfo, thiocyanate, isothiocyanate, phosphino, phosphono, and phosphate,
  more preferably from the group consisting of hydroxyl, halogen, carbonyl, aldehyde, carboxylate, carboxyl, ester, ether, carboxamide, amine, imine, cyanate, isocyanate, nitrate, nitrile, isonitrile, and combinations of two or more thereof,
  more preferably from the group consisting of hydroxyl, halogen, carbonyl, aldehyde, carboxylate, carboxyl, ester, ether, and combinations of two or more thereof, more preferably from the group consisting of hydroxyl, halogen, carbonyl, alkoxy, and combinations of two or more thereof,
  more preferably from the group consisting of hydroxyl, fluoro, chloro, bromo, (C1-C3)alkoxy, and combinations of two or more thereof,
  more preferably from the group consisting of hydroxyl, fluoro, chloro, (C1-C2)alkoxy, and combinations of two or more thereof,
  more preferably from the group consisting of hydroxyl, fluoro, chloro, methoxy, and combinations of two or more thereof,
  wherein more preferably the one or more alkylating agents are substituted with one or more hydroxyl groups.

23. The process of embodiment 16 to 21, wherein the one or more alkenes are unsubstituted, wherein preferably the one or more alkylating agents consist of one or more unsubstituted alkenes.

24. The process of any of embodiments 1 to 23, wherein the molar ratio of the one or more aliphatic organic compounds to the one or more alkylating agents ranges from 10 to 250, preferably from 20 to 150, more preferably from 30 to 100, more preferably from 35 to 80, more preferably from 40 to 60, and even more preferably from 45 to 55.

25. The process of any of embodiments 1 to 24, wherein step (b) is conducted at a temperature ranging from 50 to 250° C., preferably from 60 to 200° C., more preferably from 70 to 150° C., more preferably from 80 to 120° C., and even more preferably from 90 to 110° C.

26. The process of any of embodiments 1 to 25, wherein step (b) is conducted at a pressure comprised in the range of from 1 to 50 bar, preferably of from 4 to 40 bar, more preferably of from 8 to 35 bar, more preferably of from 12 to 30 bar, more preferably of from 14 to 29 bar, more preferably of from 16 to 28 bar, more preferably of from 18 to 27 bar, more preferably of from 20 to 26 bar, and even more preferably of from 22 to 25 bar.

27. The process of any of embodiments 1 to 26, wherein step (b) is conducted for a duration of from 0.5 to 100 h, preferably of from 1 to 80 h, more preferably of from 4 to 50 h, more preferably of from 8 to 35 h, more preferably of from 12 to 30 h, more preferably of from 15 to 26 h, and even more preferably of from 18 to 22 h.

28. The process of any of embodiments 1 to 27, wherein the process is conducted in a batch or in a continuous mode, preferably in a continuous mode.

29. The process of any of embodiments 1 to 28, wherein the one or more reactors contain the catalyst in the form of a fixed bed and/or as a fluidized bed, wherein preferably one or more of the one or more reactors contain the catalyst in the form of a fixed bed.

30. The process of any of embodiments 1 to 29, wherein the catalyst comprising one or more zeolitic materials having a BEA framework structure is provided in the form of a molding.

DESCRIPTION OF THE FIGURES

FIG. 2 further includes the respective line patterns of zeolite beta obtained from template mediated synthesis and of mordenite for comparison.

FIG. 6 further includes the respective line patterns of zeolite beta and chabazite.

EXAMPLES

Reference Example 1: Preparation of Zeolite Beta from Organotemplate-Free Synthesis 23.95 g of $NaAlO_2$ were dissolved in 812.35 g of $H_2O$, followed by addition of 9.01 g of Al-beta zeolite seed crystals (CP814C zeolite beta from Zeolyst International; calcined 5 h at 500° C. for obtaining H-form prior to use). 1154.69 g of sodium-water glass solution (26 wt.-% $SiO_2$ and 8 wt.-% $Na_2O$ from Fa. Woellner) were then slowly added to the mixture while stirring, wherein a gel is first produced which is then dissolved after further addition of the solution.

The mixture was then transferred into a 2.5 L autoclave and heated without stirring to 120° C. over a period of 3 h and then crystallized at that temperature for 117 h. After having let the reaction mixture cool to room temperature, it was filtered and the solid residue repeatedly washed with distilled water to neutralization, after which it was dried at 120° C. for 16 h thus affording 85 g of a white crystalline product. The product displayed a crystallinity grade of 90% compared to the crystallinity of the seed crystals employed in the synthesis in the 2 theta rage of 18° to 25°.

Figure 1:
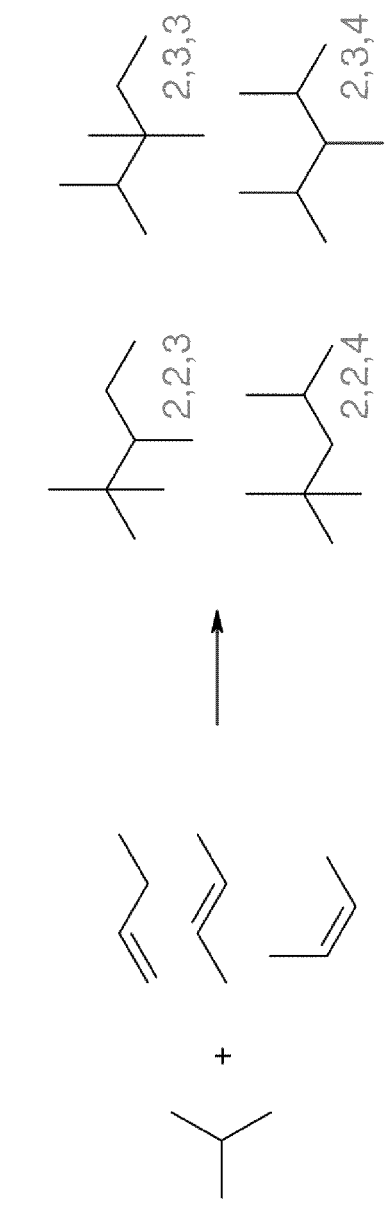
FIG. 1 schematically displays the reaction of isobutane with linear butenes and their direct reaction products.
Figure 2:
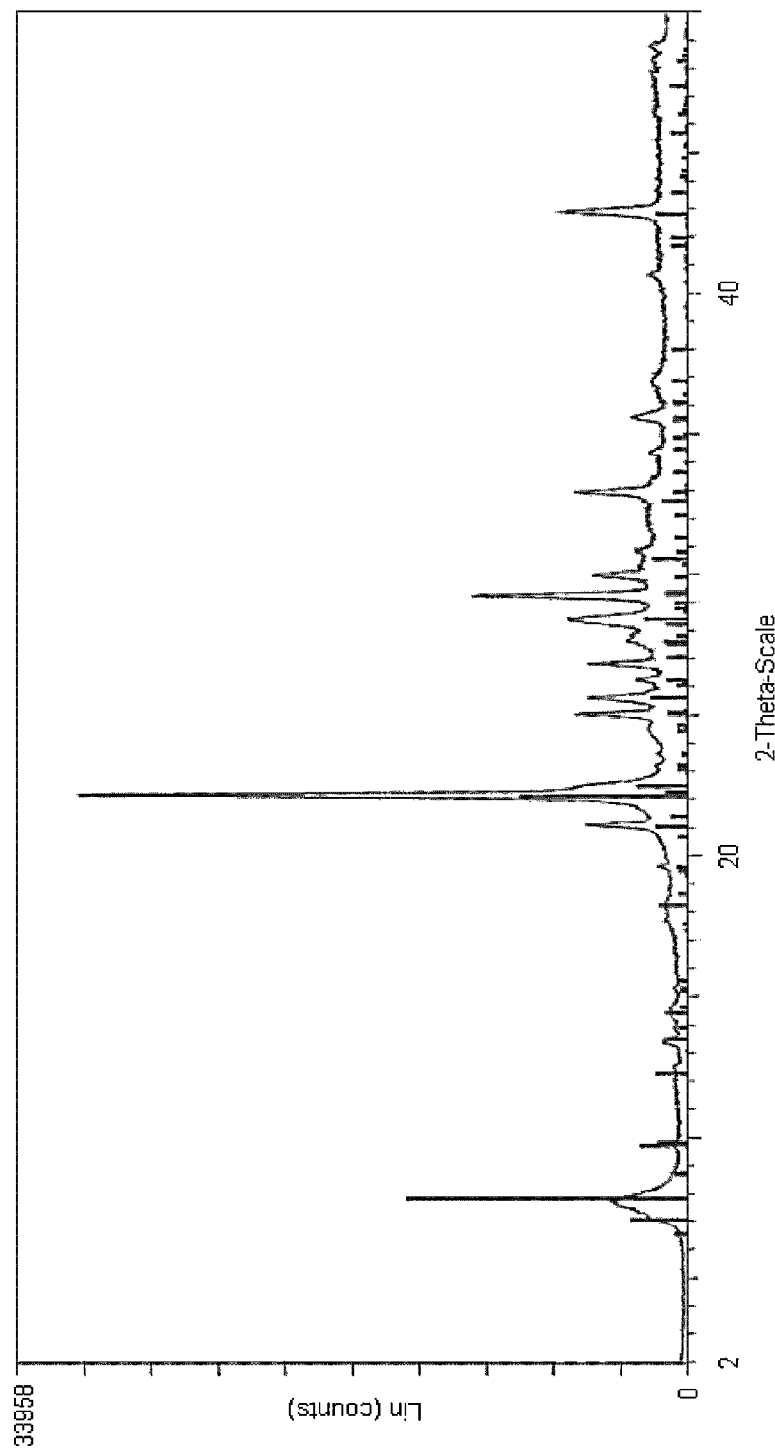
FIG. 2 shows the X-ray diffraction (XRD) pattern (measured using Cu K alpha-1 radiation) of the zeolitic material obtained from organotemplate-free synthesis according to Reference Example 2. In the figure, the diffraction angle 2 theta in ° is shown along the abscissa and the intensities are plotted along the ordinate.

In FIG. 2, the XRD of the crystalline product is displayed. In particular, the XRD pattern is typical for a BEA framework structure as obtained from organotemplate-free synthesis in view of the 2 characteristic reflections observed in the 25 to 26° 2 theta range.

Elemental analysis of the crystalline product afforded an Si:Al molar ratio of 4.8:1. Energy dispersive X-Ray (EDX) composition analysis of the sample afforded an Si:Al molar ratio of 4.9:1.

1 g of the crystalline product was then subject to two subsequent ion exchange steps using a 10 wt. % aqueous ammonium nitrate solution at 80° C., wherein the ion-exchanged material was the calcined at 350° C. for 5 h.

Figure 3:
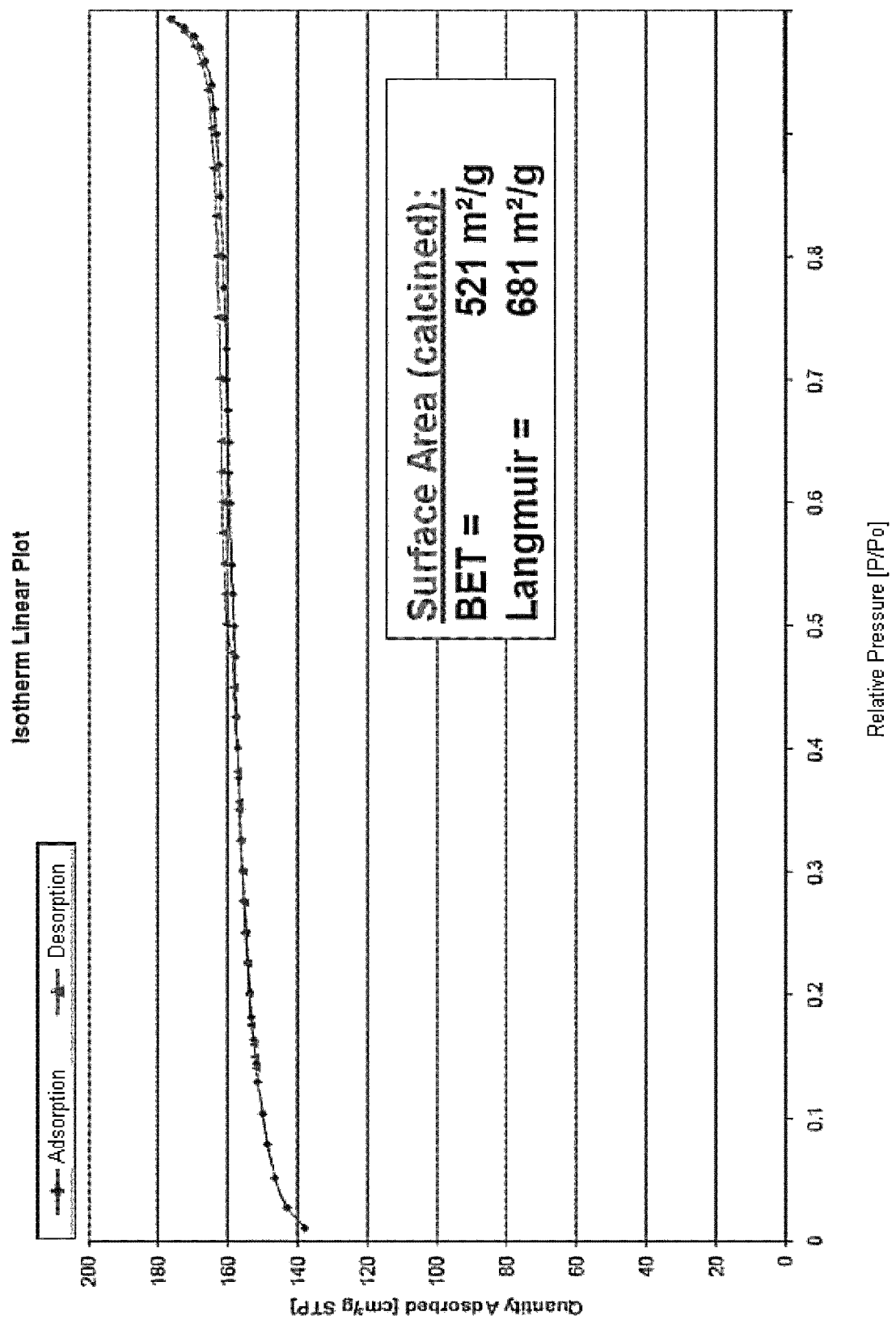
FIG. 3 shows the nitrogen adsorption isotherm of the zeolitic material obtained according to Reference Example 2. In the figure, the relative pressure $p/p°$ is plotted along the abscissa and the pore volume in $cm^3/g$ STP (standard pressure and temperature), determined according to DIN 66134 at 77 K, is plotted along the ordinate. The values for the adsorption are indicated by the symbols (♦) and the values for the desorption are indicated by the symbols (▲).

In FIG. 3, the nitrogen isotherm obtained using the ion-exchanged product is shown. In particular, the step-like curve of a type I adsorption isotherm typical of microporous solids is evident (cf. DIN 66135), indicating that the as-synthesized zeolitic material has open micropores. The evaluation of the data gave an equivalent surface of 681 $m^2/g$ according to the Langmuir method, and a BET surface area of 521 $m^2/g$.

Reference Example 2: Preparation of the H-Form of Zeolite Beta from the Product of Reference Example 1

The non-ion exchanged crystalline product of Reference Example 1 was subject to three subsequent ion exchange steps with a 0.5 M ammonium nitrate solution, respectively, after which is was calcined for 6 h at 450° C.

Reference Example 3: Preparation of Zeolite Beta from Organotemplate-Free Synthesis 332.1 g of $NaAlO_2$ were dissolved in 7578.8 g of $H_2O$, followed by addition of 62.8 g of Al-beta zeolite seed crystals (CP814C zeolite beta from Zeolyst International; H-form), after which 363.6 g of fumed silica (Aerosil® 200 from Degussa) were slowly added while stirring at 200 rpm. The mixture was then transferred into a 20 L autoclave and 8062.6 g of sodium-water glass solution (26 wt.-% $SiO_2$ and 8 wt.-% $Na_2O$ from Fa. Woellner) were then slowly added to the mixture while stirring, wherein a gel is first produced which is then dissolved after further addition of the solution.

The mixture was then heated without stirring to 120° C. over a period of 3 h and then crystallized at that temperature for 117 h. After having let the reaction mixture cool to room temperature, it was filtered and the solid residue repeatedly washed with distilled water to neutralization, after which it was dried at 120° C. for 16 h thus affording 1330 g of a white crystalline product. The product displayed a crystallinity grade of 90% compared to the crystallinity of the seed crystals employed in the synthesis in the 2 theta rage of 18° to 25°.

Elemental analysis of the crystalline product afforded an Si:Al molar ratio of 4.5:1.

As for Reference Example 1, the XRD of the crystalline product displayed an XRD pattern which is typical for a BEA framework structure as obtained from organotemplate-free synthesis in view of 2 characteristic reflections observed in the 25 to 26° 2 theta range.

Reference Example 4: Preparation of the H-Form of Zeolite Beta from the Product of Reference Example 3

The crystalline product of Reference Example 3 was subject to three subsequent ion exchange steps with a 0.5 M ammonium nitrate solution, respectively, after which is was calcined for 6 h at 450° C.

Reference Example 5: Preparation of Zeolite Beta from Organotemplate-Free Synthesis 18.28 kg of Al-beta zeolite seed crystals (CP814C zeolite beta from Zeolyst International; calcined prior to use for obtaining H– from thereof) were suspended in 100 kg of distilled water, and the solution was then further stirred for 30 min at 100 rpm. In a separate vessel, 24.75 kg of $NaAlO_2$ were dissolved in 399.6 kg of distilled water, and the solution was then further stirred for 30 min at 50 rpm. The aqueous suspension of the seed crystals was then added to the sodium aluminate solution under stirring, and the empty vessel then rinsed with 20 L distilled water, wherein the rinsing solution was then added to the mixture. 555.27 kg g of sodium-water glass solution (26 wt.-% $SiO_2$ and 8 wt.-% $Na_2O$ from Fa. Woellner) were then continuously added over 1 h to the mixture under stirring at 25 rpm, and the empty vessel then rinsed with 10 L distilled water, wherein the rinsing solution was then added to the mixture. 96.21 kg of an aqueous solution of colloidal silica (40%; Ludox AS 40 from Grace) was then added to mixture under stirring, and the empty vessel then rinsed with 5 L distilled water, wherein the rinsing solution was then added to the mixture.

The mixture was then heated to 120° C. over a period of 3 h while stirring at 25 rpm and then crystallized at that temperature for 84 h. After having let the reaction mixture cool to room temperature, it was filtered and the solid residue repeatedly washed with distilled water to neutralization, after which it was dried at 120° C. thus affording 122.523 kg of a white crystalline product. The product displayed a crystallinity grade of 71% compared to the crystallinity of the seed crystals employed in the synthesis in the 2 theta rage of 18° to 25°.

As for Reference Examples 1 and 3, the XRD of the crystalline product displayed an XRD pattern which is typical for a BEA framework structure as obtained from organotemplate-free synthesis in view of 2 characteristic reflections observed in the 25 to 26° 2 theta range.

Elemental analysis of the crystalline product afforded an Si:Al:Na molar ratio of 0.9:0.2:0.2. The Si:Al molar ratio of the product was thus 4.5:1.

The nitrogen isotherm in accordance with DIN 66135 was determined, wherein the evaluation of the data gave an equivalent surface of 643 $m^2/g$ according to the Langmuir method, and a BET surface area of 471 $m^2/g$.

100 g of the crystalline product was then added to 1 kg of a 10 wt. % aqueous ammonium nitrate solution in which it was stirred for 2 h at 80° C., the solid then filtered off and washed with distilled water until the filtrate was free of nitrate. The ion exchange step was then repeated, after which the product was dried at 120° C. overnight, for affording 90 g of the ion-exchanged crystalline product.

Elemental analysis of the ion-exchanged product afforded an Si:Al:Na molar ratio of 1.17:0.22:0.002. The Si:Al molar ratio of the product was thus 5.3:1.

Reference Example 6: Preparation of Zeolite Beta from Organotemplate-Free Synthesis 332.1 g of $NaAlO_2$ were dissolved in 7578.8 g of $H_2O$, followed by addition of 62.8 g of Al-beta zeolite seed crystals (CP814C zeolite beta from Zeolyst International; H-form), after which 363.6 g of fumed silica (Aerosil® 200 from Degussa) were slowly added while stirring at 200 rpm. The mixture was then transferred into a 20 L autoclave and 8062.6 g of sodium-water glass solution (26 wt.-% $SiO_2$ and 8 wt.-% $Na_2O$ from Fa. Woellner) were then slowly added to the mixture while stirring at 200 rpm, wherein a gel is first produced which is then dissolved after further addition of the solution.

The mixture was then heated without stirring to 120° C. over a period of 3 h and then crystallized at that temperature for 117 h. After having let the reaction mixture cool to room temperature, it was filtered and the solid residue repeatedly washed with distilled water to neutralization, after which it was dried at 120° C. for 16 h thus affording 1370 g of a white crystalline product. The product displayed a crystallinity grade of 82% compared to the crystallinity of the seed crystals employed in the synthesis in the 2 theta rage of 18° to 25°.

Elemental analysis of the ion-exchanged product afforded an Si:Al:Na molar ratio of 1.07:0.24:0.23. The Si:Al molar ratio of the product was thus 4.5:1.

As for Reference Examples 1, 3, and 5, the XRD of the crystalline product displayed an XRD pattern which is typical for a BEA framework structure as obtained from organotemplate-free synthesis in view of 2 characteristic reflections observed in the 25 to 26° 2 theta range.

650 g of the crystalline product was then added to 6.5 kg of a 10 wt. % aqueous ammonium nitrate solution in which it was stirred for 2 h at 80° C., the solid then filtered off and washed with distilled water until the filtrate was free of nitrate. The ion exchange step was then repeated, after which the product was dried at 120° C. for 16 h. The product was then heated to 450° C. using a ramp of 1° C./min and then calcined at that temperature for 5 h, thus affording 575 g of the calcined ion-exchanged crystalline product.

Elemental analysis of the calcined ion-exchanged product afforded an Si:Al:Na molar ratio of 1.1:0.25:0.004. The Si:Al molar ratio of the product was thus 4.4:1.

The calcined ion-exchanged product displayed a crystallinity grade of 86% compared to the crystallinity of the seed crystals employed in the initial synthesis in the 2 theta rage of 18° to 25°.

60 g of the calcined ion-exchanged crystalline product was then added to 300 g of a 2% $HNO_3$ solution in which it was stirred for 2 h at 60° C., the solid then filtered off and washed with distilled water until the filtrate was free of nitrate. The product was then dried at 120° C. for 16 h, and then heated to 450° C. using a ramp of 1° C./min and calcined at that temperature for 5 h, thus affording a white crystalline product.

Elemental analysis of the final product afforded an Si:Al:Na molar ratio of 1.25:0.19:0.01. The Si:Al molar ratio of the product was thus 6.6:1.

The calcined ion-exchanged product displayed a crystallinity grade of 52% compared to the crystallinity of the seed crystals employed in the initial synthesis in the 2 theta rage of 18° to 25°.

Reference Example 7: Dealumination of Zeolite Beta from Reference Example 6 by Acid Treatment 45 g of the zeolite beta obtained from Reference Example 6 was then added to 225 mL of a 2% $HNO_3$ solution in which it was stirred for 2 h at 60° C., the solid then filtered off and washed with distilled water until the filtrate was free of nitrate. The product was then dried at 120° C. for 16 h, and then heated to 450° C. using a ramp of 1° C./min and calcined at that temperature for 5 h, thus affording 44 g of a white crystalline product.

Elemental analysis of the final product afforded an Si:Al:Na molar ratio of 1.35:0.16:0.001. The Si:Al molar ratio of the product was thus 8.4:1.

The calcined ion-exchanged product displayed a crystallinity grade of 52% compared to the crystallinity of the seed crystals employed in the initial synthesis in the 2 theta rage of 18° to 25°.

Reference Example 8: Preparation of Zeolite Beta from Organotemplate-Free Synthesis 19.91 kg of Al-beta zeolite seed crystals (CP814C zeolite beta from Zeolyst International; calcined) were suspended in 100 kg of distilled water, and the solution was then further stirred for 30 min at 100 rpm. In a separate vessel, 26.96 kg of NaAlO$_2$ were dissolved in 443.15 kg of distilled water, and the solution was then further stirred for 30 min at 50 rpm. The aqueous suspension of the seed crystals was then added to the sodium aluminate solution under stirring, and the empty vessel then rinsed with 20 L distilled water, wherein the rinsing solution was then added to the mixture. 620.15 kg g of sodium-water glass solution (26 wt.-% SiO$_2$ and 8 wt.-% Na$_2$O from Fa. Woellner) were then continuously added over 1 h to the mixture under stirring at 25 rpm, and the empty vessel then rinsed with 10 L distilled water, wherein the rinsing solution was then added to the mixture. 94.78 kg of an aqueous solution of colloidal silica (40%; Ludox AS 40 from Grace) was then added to mixture under stirring, and the empty vessel then rinsed with 5 L distilled water, wherein the rinsing solution was then added to the mixture.

The mixture was then heated to 120° C. over a period of 3 h while stirring at 25 rpm and then crystallized at that temperature for 79 h. After having let the reaction mixture cool to room temperature, it was filtered and the solid residue repeatedly washed with distilled water to neutralization, after which it was dried at 120° C. thus affording 117 kg of a white crystalline product. The product displayed a crystallinity grade of 72% compared to the crystallinity of the seed crystals employed in the synthesis in the 2 theta rage of 18° to 25°.

As for Reference Examples 1, 3, 5, and 6, the XRD of the crystalline product displayed an XRD pattern which is typical for a BEA framework structure as obtained from organotemplate-free synthesis in view of 2 characteristic reflections observed in the 25 to 26° 2 theta range.

Elemental analysis of the product afforded an Si:Al:Na molar ratio of 1.07:0.23:0.22. The Si:Al molar ratio of the product was thus 4.7:1.

The nitrogen isotherm in accordance with DIN 66135 was determined, wherein the evaluation of the data gave an equivalent surface of 611 m$^2$/g according to the Langmuir method.

25 kg of the crystalline product was then added to 250 kg of a 10 wt. % aqueous ammonium nitrate solution in which it was stirred for 2 h at 80° C., the solid then filtered off and washed with distilled water until the filtrate was free of nitrate. The ion exchange step was then repeated, after which the product was dried at 120° C. for 16 h. The dried product was then heated to 500° C. using a ramp of 1° C./min and calcined at that temperature for 5 h. The product displayed a crystallinity grade of 74% compared to the crystallinity of the seed crystals employed in the synthesis in the 2 theta rage of 18° to 25°.

Elemental analysis of the ion-exchanged product afforded an Si:Al:Na molar ratio of 1.28:0.22:0.001. The Si:Al molar ratio of the product was thus 5.8:1.

The nitrogen isotherm of the ion-exchanged product was determined in accordance with DIN 66135, wherein the evaluation of the data gave an equivalent surface of 636 m$^2$/g according to the Langmuir method.

Reference Example 9: Dealumination of Zeolite Beta from Reference Example 8 by Steam and Acid Treatment The product of Reference Example 8 was subject to a steam treatment for 1 h at 700° C. in a nitrogen atmosphere containing 10% H$_2$O. The steam treated material was then subject to three subsequent acid treatment steps with a 2% HNO$_3$ solution in which it was stirred for 2 h at 60° C., the solid then filtered off and washed with distilled water until the filtrate was free of nitrate, respectively. The product was then dried at 120° C. for 16 h, and then heated to 450° C. using a ramp of 1° C./min and calcined at that temperature for 5 h, thus affording a white crystalline product displaying an Si:Al molar ratio of 17.9:1.

Reference Example 10: Synthesis of Zeolite Beta According to U.S. Pat. No. 5,824,835 A 513.23 grams of colloidal silica (30 wt.-%, Ludox SM-30), 574.77 grams of tetraethylammonium hydroxide (35 wt.-%), 24.61 grams of aluminum hydroxide and 0.68 grams of water were added to a vessel and stirred at 700 rpm for 1 hour. The resulting mixture was transferred to an autoclave and heated at a rate of 2° C./minute to 100° C. The mixture was stirred at 100° C. and 60 rpm for 48 hours. The autoclave was allowed to cool to room temperature, opened and 538.9 grams of aqueous barium hydroxide (5 wt.-%) was added followed by addition of 47.94 grams of aqueous potassium hydroxide (10 wt.-%). The autoclave was then sealed and the resulting mixture was heated at a rate of 2° C./minute to 150° C. The mixture was stirred at 150° C. and 60 rpm for 168 hours. The product was then filtered and dried at 110° C. overnight.

Figure 6:
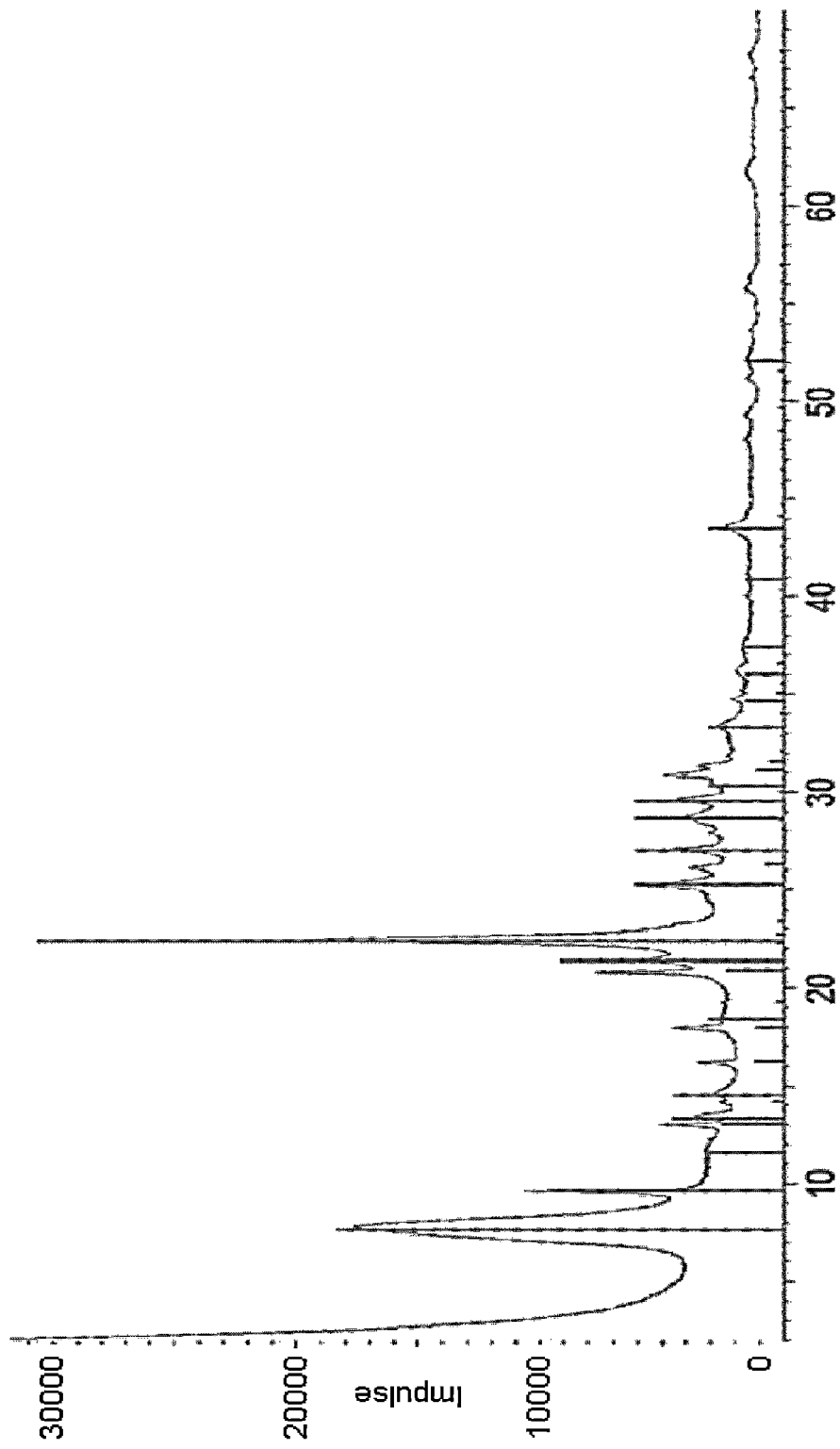
FIG. 6 shows the X-ray diffraction (XRD) pattern (measured using Cu K alpha-1 radiation) of the zeolitic material obtained according to Reference Example 10. In the figure, the diffraction angle 2 theta in ° is shown along the abscissa and the intensities are plotted along the ordinate.

The dried zeolitic material was treated with 1M ammonium chloride whose pH was adjusted to 8 over 1 hour at 60° C. The ion exchange was repeated twice. The product was then collected by centrifugation, washed with water and collected again by centrifugation. The washing/centrifugation were repeated once. The resulting zeolitic material was dried for 16 hours at 110° C. The dry exchanged product was heated up to 538° C. in a stream of dry nitrogen at 2° C. per minute and held for 3 hours. The temperature was lowered to 250° C. and the atmosphere was switched to air after which the temperature was raised again to 538° C. at 2° C. per minute and held for three hours. The crystallinity of the obtained calcined material was found to be 76% and the product contained minor amounts of CHA zeolitic material as evidenced in the XRD (see FIG. 6 for the XRD of Reference Example 10).

Elemental analysis of the ion-exchanged product afforded an Si:Al:K:Ba:C molar ratio of 1:0.123:0.00378:0.0014:0.006. The Si:Al molar ratio of the product was thus 8.1:1.

Example 1: Alkylation of Isobutane with but-1-Ene

The catalysts (500 mg) from Reference Examples 2, 4, 5, 7, and 9 were respectively activated at 250° C. and subsequently placed in a 100 mL Parr reactor that was closed immediately and purged with nitrogen. As comparative examples, two commercial zeolite beta samples were employed, both obtained from a synthesis methodology employing an organotemplate, wherein the first displayed an Si:Al molar ratio of 12.5 (CP811 from PQ Corporation), and the second an Si:Al molar ratio of 30 (H-beta from Südchemie). The reactor was cooled on ice and liquid isobutane was added via a 31.4 mL compressed air driven plunger that was cooled at 15° C. to ensure that isobutane is in its liquid state. Subsequently gaseous 1-butene was added using a 49.1 mL plunger that was not cooled. The lines were subsequently purged with nitrogen to ensure that the entire olefin was transferred to the reactor. Reactions were carried out at 70° C. to 100° C. while stirring the slurry. After completion of the reaction, the reactor was cooled on ice and the gases were released. Subsequently n-decane was added to the reactor to dilute the reaction products. Reactions were analyzed using a GC-FID instrument with tetradecane as standard.

The alkylation of isobutane with 1-butene was tested with an olefin/paraffin ratio of 1/50. Initially, the commercial zeolite beta samples were tested, where the best catalyst provided 149 $mg_{product}/g_{cat}$ at 42% $C_8$ selectivity. As may be taken from FIG. 4, zeolite beta from organotemplate-free synthesis as obtained from Reference Examples 2, 4, and 5 displaying Si/Al ratios ranging from 4.5 to 5.3 provided significantly higher activity with up to 407 $mg_{product}/g_{cat}$ compared to the commercial samples from templated synthesis. Furthermore, as may be taken from FIG. 5, zeolite beta from organotemplate-free synthesis as obtained from Reference Examples 2, 4, and 5 further provided the highest $C_8$ selectivites. Dealumination of zeolites from organotemplate-free synthesis as achieved in Reference Example 7 and 9 resulted in both lower activity and lower $C_8$ selectivity than for the untreated zeolites from Reference Examples 2, 4, and 5.

Figure 4:
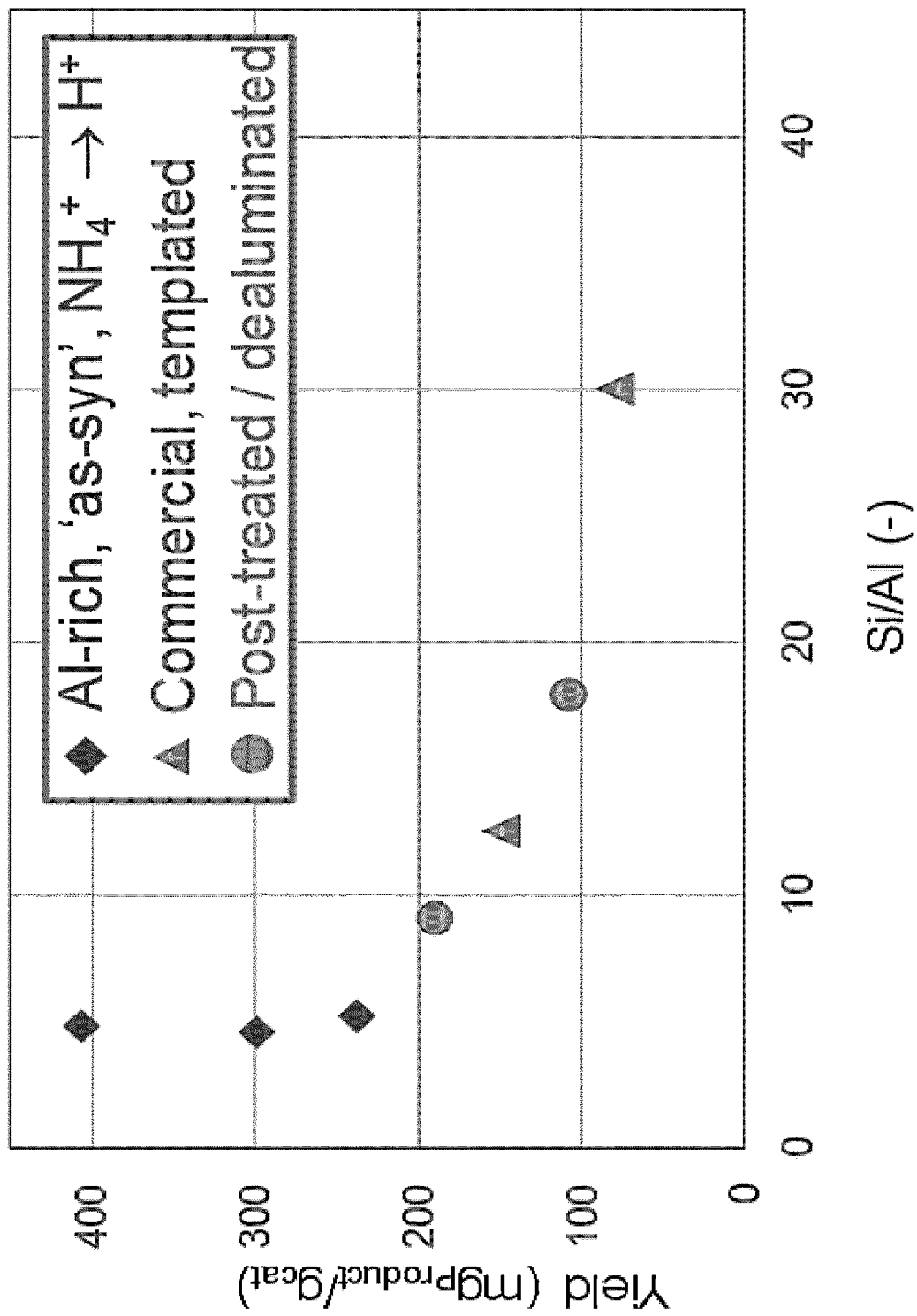
FIG. 4 shows the results from experimental testing of the catalyst samples from Reference Examples 2, 4, 5, 7, and 9 in the alkylation of isobutane with but-1-ene as obtained according to Example 1. In the figure, the Si:Al molar ratio of the respective sample is plotted along the abscissa and the yield in alkylation product in mg relative to the amount of catalyst in g ($mg_{product}/g_{cat}$), is plotted along the ordinate. The values obtained for Reference Examples 2, 4, and 5 are indicated by the symbols (♦), those obtained for the dealuminated samples of Reference Examples 7 and 9 are indicated by the symbols (●), and those obtained for the commercial zeolite beta samples are indicated by the symbols (▲).
Figure 5:
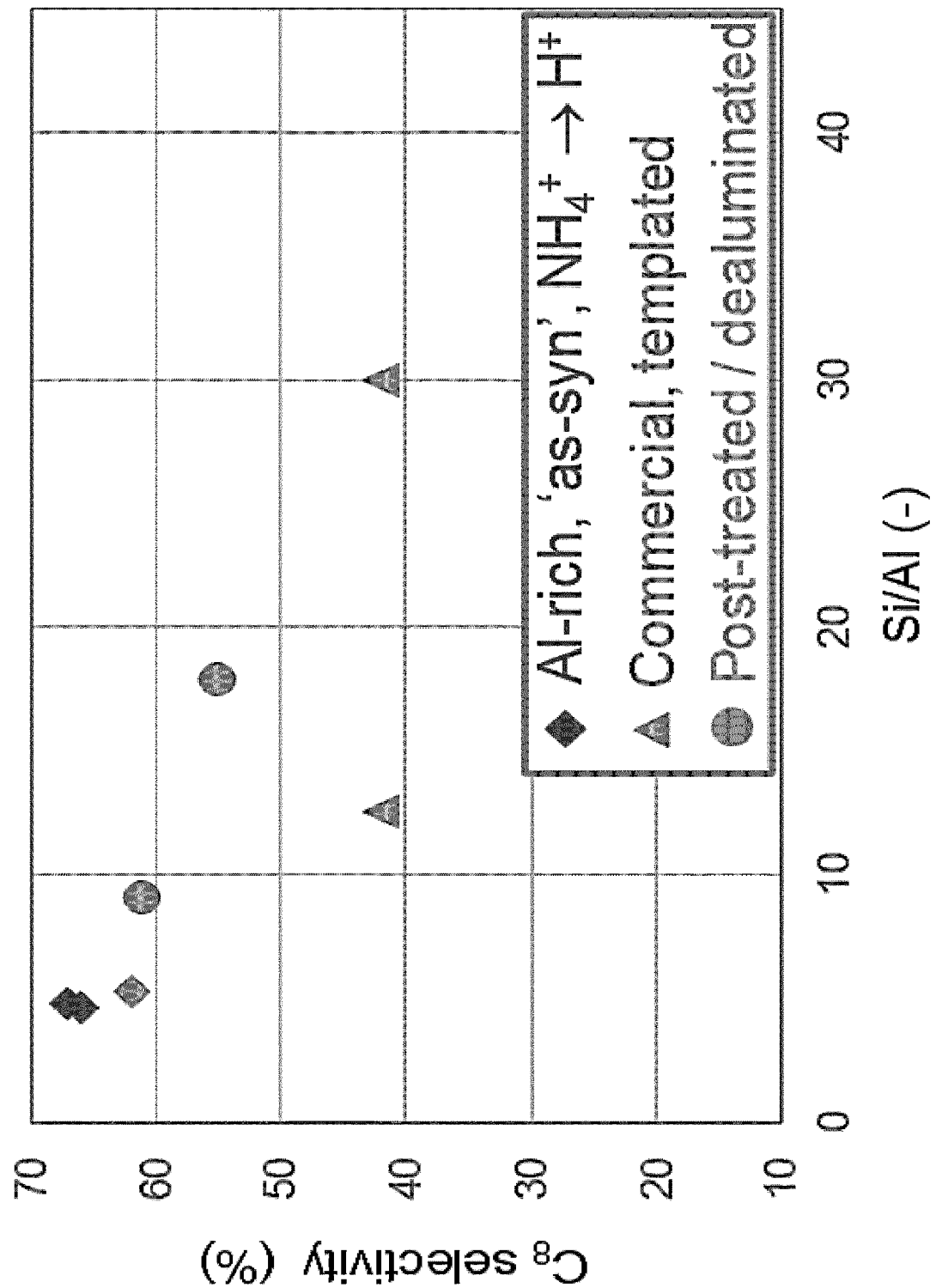
FIG. 5 shows the results from experimental testing of the catalyst samples from Reference Examples 2, 4, 5, 7, and 9 in the alkylation of isobutane with but-1-ene as obtained according to Example 1. In the figure, the Si:Al molar ratio of the respective sample is plotted along the abscissa and the selectivity of the respective catalyst samples towards the $C_8$-alkylation products expressed in % relative to 100% of the alkylation product is plotted along the ordinate. The values obtained for Reference Examples 2, 4, and 5 are indicated by the symbols (♦), those obtained for the dealuminated samples of Reference Examples 7 and 9 are indicated by the symbols (●), and those obtained for the commercial zeolite beta samples are indicated by the symbols (▲).

As may be further taken from the results in FIG. 4, a clear relationship between the Si:Al ratio and the activity of the zeolite beta catalyst may be observed, wherein the activity decreases with decreasing Si:Al ratio, independently as to whether the zeolite was obtained from templated or from organotemplate-free synthesis, or whether the Si:Al ratio was achieved by subsequent dealumination of the zeolite beta after synthesis thereof. However, it has quite surprisingly been found that although a similar relationship is observed in the results in FIG. 5 for the $C_8$-selectivity of the respective catalysts, zeolite beta as obtained from organotemplate-free synthesis displays a substantially higher selectivity than the catalysts obtained from templated synthesis at comparable Si:Al ratios, in particular for those samples displaying low Si:Al molar ratios. In particular, it has quite unexpectedly been found that compared to the commercial zeolite beta samples obtained from templated synthesis, which are practically insensitive to variations in the $C_8$-selectivity, the catalyst samples obtained from organotemplate-free synthesis do not only display a substantially higher selectivity, but also show a strong relationship between the Si:Al molar ratio and the $C_5$-selectivity of the samples. In particular, the samples from Reference Examples 2 and 4 with Si:Al molar ratios in the range of 4 to 5 afford $C_8$-selectivities which are almost twice as high as observed for commercial zeolite beta which is obtained from templated synthesis.

Furthermore, Reference Example 10, which represents the teaching of prior art document U.S. Pat. No. 5,824,835 A, was also evaluated in the alkylation of isobutane with but-1-ene according to Example 1, the results of which are given in Table 1 below, together with the results obtained using the zeolite from organotemplate-free synthesis according Reference Example 2.

TABLE 1

Comparison of alkylation of isobutane with but-1-ene with zeolites from Reference Examples 10 and 2.

| | yield [mg/g catalyst] | selectivity [%] | | |
| --- | --- | --- | --- | --- |
| | | ≤$C_7$ | $C_8$ | ≥$C_9$ |
| Reference Ex. 10 | 154 | 7.9 | 52 | 40.1 |
| Reference Ex. 2 | 407 | 10 | 69.4 | 20.6 |

Thus, as may be taken from the results in Table 1 the results of the present invention are also confirmed in view of prior art document U.S. Pat. No. 5,824,835 A, which specifically teaches the use of zeolite beta from conventional (templated) synthesis in the alkylation of isobutane with butene-2. In particular, as may be taken from the results with regard to the $C_8$-selectivity, the inventive process using Reference Example 2 which is a zeolite beta obtained from organotemplate-free synthesis achieves a considerably higher selectivity compared to the $C_8$ selectivity achieved with Reference Example 10, which confirms the results and general tendencies displayed in FIG. 5.

Accordingly, it has surprisingly been found that the use of zeolite beta from organotemplate-free synthesis in a process for the alkylation of isobutane with 1-butene affords considerably better results than with commercial zeolite beta with regard to both activity and selectivity, in particular towards $C_8$-alkane products. Furthermore, it has quite unexpectedly been found that this is not only dependent on the lower Si:Al molar ratios which may be afforded using the organotemplate-free synthetic methodology, but is further due to the unique structure of the zeolite beta materials obtained from said method, in particular in view of the outstanding and completely unexpected selectivities which may be achieved with regard to the desired $C_8$-alkane products.

CITED PRIOR ART DOCUMENTS

Feller, A. et al. in Journal of Catalysis, 2004, Vol. 224, pp. 80-93
Dalla Costa, B. O. et al. in Applied Catalysis A 2010, Vol. 385, pp. 144-152
Corma, A. et al. in Applied Catalysis A 1994, Vol. 119, pp. 83-96
WO 2012/137133 A
Xiao et al., Chem. Mater. 2008, 20, pp. 4533-4535
WO 2010/146156 A
Majano et al., Chem. Mater. 2009, 21, pp. 4184-4191
U.S. Pat. No. 4,992,616 A
U.S. Pat. No. 5,824,835 A
Nivarthy, G. S. et al. in Microporous and Mesoporous Materials 2000, vol. 35-36, pages 75-87
Nivarthy, G. S. et al. in Microporous and Mesoporous Materials 1998. vol. 22, no. 1-3, pages 379-388
Yuki Kato et al. in Journal of the Japan Petroleum Institute 2013, vol. 56, no. 5, pages 349-355

The invention claimed is:

1. A process for the alkylation of an aliphatic organic compound, the process comprising:
  preparing one or more zeolite beta materials in a synthetic process which does not employ an organotemplate as a structure directing agent, the synthetic process comprising the steps of:
    1) preparing a mixture comprising seed crystals, one or more sources for $SiO_2$, and one or more sources for $Al_2O_3$; and
    2) crystallizing the mixture to produce the one or more zeolite beta materials;
  providing a catalyst comprising the one or more zeolite beta materials,
    wherein the zeolite beta material comprises $SiO_2$ and $Al_2O_3$, and
    wherein Si is a tetravalent element and Al is a trivalent element; and contacting the catalyst with one or more aliphatic organic compounds in the presence of one or more alkylating agents to obtain one or more alkylated organic compounds;

wherein the Si:Al molar ratio of the one or more zeolite beta materials ranges from 4.1 to 6;

wherein the one or more zeolite beta materials contains H+ as counterions;

wherein the one or more zeolite beta materials contains 0.5 wt.-% or less of alkali metals based on 100 wt.-% of $SiO_2$, wherein the one or more aliphatic organic compounds have the formula

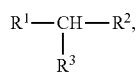

wherein $R^1$, $R^2$, and $R^3$ are each independently an alkyl group, and wherein the one or more alkylating agents comprise one or more alkenes selected from the group consisting of C2-C6 alkenes and mixtures thereof.

2. The process of claim 1, wherein the one or more zeolite beta materials are non-calcined.

3. The process of claim 1, wherein the one or more zeolite beta materials have an X-ray diffraction pattern comprising the following reflections:

9-29% intensity at a diffraction angle of 21.06-21.26°;
100% intensity at a diffraction angle of 22.11-22.31°;
10-30% intensity at a diffraction angle of 25.01-25.21°;
8-28% intensity at a diffraction angle of 26.77-26.97°;
12-32% intensity at a diffraction angle of 28.38-28.58°;
27-47% intensity at a diffraction angle of 29.22-29.42°;
7-27% intensity at a diffraction angle of 29.99-30.19°;
9-29% intensity at a diffraction angle of 32.85-33.25°; and
11-31% intensity at a diffraction angle of 42.86-43.26°;
wherein 100% relates to the intensity of the maximum peak in the X-ray powder diffraction pattern, and
wherein the diffraction angles are in terms of 2θ [Cu K(alpha 1)].

4. The process of claim 3, wherein the X-ray diffraction pattern further comprises the following reflection:

6-26% intensity at a diffraction angle of 25.54-25.74°.

5. The process of claim 1, wherein $R^1$, $R^2$, and $R^3$ are each independently a substituted C1-C3 alkyl group.

6. The process of claim 1, wherein the one or more alkylating agents comprise one or more alkenes selected from the group consisting of C3-C5 alkenes and mixtures thereof.

7. The process of claim 1, wherein a molar ratio of the one or more aliphatic organic compounds to the one or more alkylating agents ranges from 10 to 250.

8. The process of claim 1, wherein the process is conducted in a batch or in a continuous mode.

9. The process of claim 1, wherein the one or more aliphatic organic compounds is isobutane; wherein the one or more alkylating agents is 1-butene; and wherein the one or more alkylated organic compounds comprises from 52 mol % to 69.4 mol % alkylated organic compounds having 8 carbon atoms relative to 100 mol % of the one or more alkylated organic compounds.

10. The process of claim 1, wherein the Si:Al molar ratio of one or more of the one or more zeolite beta materials ranges from 4.1 to 5.5.

11. The process of claim 1, wherein the Si:Al molar ratio of one or more of the one or more zeolite beta materials ranges from 4.3 to 5.5.

12. The process of claim 1, wherein the Si:Al molar ratio of one or more of the one or more zeolite beta materials ranges from 4.3 to 5.

* * * * *